(12) United States Patent
Qiao et al.

(10) Patent No.: US 11,471,980 B2
(45) Date of Patent: Oct. 18, 2022

(54) METHOD AND SYSTEM FOR ULTRAFAST LASER-BASED MATERIAL REMOVAL, FIGURING AND POLISHING

(71) Applicants: Jie Qiao, Rochester, NY (US); Lauren L. Taylor, Medford, NJ (US)

(72) Inventors: Jie Qiao, Rochester, NY (US); Lauren L. Taylor, Medford, NJ (US)

(73) Assignee: Rochester Institute of Technology, Rochester, NY (US)

( * ) Notice: Subject to any disclaimer, the term of this patent is extended or adjusted under 35 U.S.C. 154(b) by 0 days.

(21) Appl. No.: 16/999,891

(22) Filed: Aug. 21, 2020

(65) Prior Publication Data

US 2021/0053160 A1 Feb. 25, 2021

Related U.S. Application Data

(60) Provisional application No. 62/889,811, filed on Aug. 21, 2019.

(51) Int. Cl.
*B23K 26/40* (2014.01)
*B23K 26/082* (2014.01)
(Continued)

(52) U.S. Cl.
CPC .......... *B23K 26/40* (2013.01); *B23K 26/0624* (2015.10); *B23K 26/073* (2013.01);
(Continued)

(58) Field of Classification Search
CPC .. B23K 26/40; B23K 26/0624; B23K 26/082; B23K 26/354; B23K 26/3576;
(Continued)

(56) References Cited

U.S. PATENT DOCUMENTS 6,132,424 A   10/2000 Tang
6,156,030 A *  12/2000 Neev ............... B23K 26/53
                                                      433/29

(Continued)

FOREIGN PATENT DOCUMENTS

EP    3511106 A1    7/2019
WO  2015189600 A2   12/2015

OTHER PUBLICATIONS

Dou, Kai, Robert Parkhill, Jack Wu, and Edward Knobbe; "Surface Microstructuring of Aluminum Alloy 2021 Using Femtosecond Excimer Laser Irradiation;" Jul./Aug. 2001; IEEE Journal on Selected Topics in Quantum Electronics, vol. 7, No. 4; pp. 567-578 (Year: 2001).*

(Continued)

*Primary Examiner* — Sang Y Paik
*Assistant Examiner* — Erwin J Wunderlich
(74) *Attorney, Agent, or Firm* — Bond Schoeneck & King, PLLC; Joseph M. Noto

(57) ABSTRACT

The disclosure relates to methods and systems incorporating physical modeling to identify the ultrafast laser/material interaction mechanisms and the impact of laser parameters, to optimize implementation of ultrafast laser-based processing for a given material. The process determines a laser fluence near the ablation threshold for a given material and given pulse duration. The repetition rate, scanning speed and scanning strategy are subsequently optimized to minimize heat accumulation, having an operable line scan overlap between 50% to 85% for achieving smooth ultrafast-laser polishing, while maintaining an optic-quality surface.

19 Claims, 19 Drawing Sheets

(51) Int. Cl.
B23K 26/352 (2014.01)
B23K 26/36 (2014.01)
B23K 26/0622 (2014.01)
B23K 26/073 (2006.01)
B23K 26/354 (2014.01)
B23K 103/00 (2006.01)
A61B 18/00 (2006.01)

(52) U.S. Cl.
CPC .......... *B23K 26/082* (2015.10); *B23K 26/354* (2015.10); *B23K 26/3576* (2018.08); *B23K 26/36* (2013.01); *A61B 2018/00577* (2013.01); *A61B 2018/00625* (2013.01); *B23K 2103/52* (2018.08); *B23K 2103/54* (2018.08)

(58) Field of Classification Search
CPC .............. B23K 26/073; B23K 2103/52; B23K 2103/54; B23K 26/362; A61B 2018/00625; A61B 2018/00577
USPC .................................................. 219/121.69
See application file for complete search history.

(56) References Cited

U.S. PATENT DOCUMENTS

| | | | |
|---|---|---|---|
| 6,920,765 | B2 | 7/2005 | Menapace et al. |
| 9,457,432 | B2* | 10/2016 | Denney .................... B23K 9/23 |
| 9,915,791 | B2 | 3/2018 | Woodward et al. |
| 10,688,597 | B2 | 6/2020 | Miller |
| 2002/0125230 | A1* | 9/2002 | Haight .................... A61F 9/0084 219/121.69 |
| 2004/0155017 | A1* | 8/2004 | Hunt .................... B23K 26/361 219/121.69 |
| 2005/0226287 | A1 | 10/2005 | Shah et al. |
| 2006/0219676 | A1 | 10/2006 | Taylor et al. |
| 2008/0070378 | A1 | 3/2008 | Yeo |
| 2009/0224178 | A1 | 9/2009 | Champonnois et al. |
| 2012/0196454 | A1* | 8/2012 | Shah .................... B23K 26/082 438/795 |
| 2014/0227889 | A1* | 8/2014 | Shah ...................... B23K 26/40 219/121.72 |
| 2015/0091215 | A1 | 4/2015 | Reetz et al. |
| 2018/0169791 | A1* | 6/2018 | Miller ................ B23K 26/3576 |
| 2018/0373159 | A1 | 12/2018 | Smakman et al. |

OTHER PUBLICATIONS

Heidrich, S., E. Willenborg, and A. Richmann; "Development of a Laser Based Process Chain for Manufacturing Freeform Optics;" 2011; Physics Procedia, 12; pp. 519-528 (Year: 2011).*

Ma, C.P., Y.C. Guan, and W. Zhou; "Laser polishing of additive manufacture Ti alloys;" Feb. 23, 2017; Optics and Lasers in Engineering 93; p. 171-177 (Year: 2017).*

Kong, W., et al., "Enhancing Perovskite Solar Cell Performance through Femtosecond Laser Polishing," RRL Solar, https://onlinelibrary.wiley.com/doi/abs/10.1002/solr.202000189; May 8, 2020; Abstract provided.

"Laser Polishing of Glass and Plastics," Fraunhofer Institute for Laser Technology website, https://www.ilt.fraunhofer.de/en/media-center/brochures/brochure-Polishing-with-Laser-Radiation.html; printed Aug. 10, 2020.

Schwarz, S., et al, "Fabrication of a High-Quality Axicon by Femtosecond Laser Ablation and CO2 Laser Polishing for quasi-Bessel Beam Generation," Optics Express, Sep. 3, 2018, https://pubmed.ncbi.nlm.nih.gov/30184982/; Absract provided.

Faehnle, O., et al, "Closed-loop laser polishing using in-process surface finish metrology," Applied Optics, vo. 57, issue 4, Feb. 2018, http://www.loft.optics.arizona.edu/documents/journal_articles/Closedloop_Laser_Polishing_AO_2018.

Xu, G., et al, "Simulation and experiment of femtosecond laser polishing quartz material," Integrated Ferroelectrics, vol. 181, issue 1, 2017 https://www.tandfonline.com/doi/abs/10.1080/10584587.2017.1352332?src=recsys&journalCode=ginf20.

Weingarten, C., et al, "Laser polishing and laser shape correction of optical glass," Journal of Laser Applications, vol. 29, issue 1, Feb. 2017 https://lia.scitation.org/doi/10.2351/1.4974905.

Heidrich, S. et al, "Development of a Laser Based Process Chain for Manufacturing Freeform Optics," Physics Procedia, vol. 12, 2011, https://core.ac.uk/reader/82569282.

Taylor, L.L., et al. "Femtosecond Laser Polishing of Germanium towards Freeform Fabrication [Invited]." Optical Materials Express 9 (11), 4165-4177 (2019).

Mishchik, K., et al., "High-efficiency femtosecond ablation of silicon with GHz repetition rate laser source," Opt. Lett., 44, 2193-2196 (2019).

Taylor, L., et al. "Predicting Femtosecond Laser Processing of Silicon via Integrating Thermal and Two-Temperature Models," Optics Materials Express, Optical Materials Express 8 (3) 648-658 (2018).

Taylor, L., et al., "Optimization of femtosecond laser processing of silicon via numerical modeling," Optics Materials Express, 6 (9), 2745-2758 (2016).

Taylor, L., et al., "Femtosecond laser polishing of germanium [Invited]", Optical Materials Express, vol. 9, No. 1, Nov. 2019, pp. 4165-4177.

Taylor et al., Integrating two-temperature and classical heat accumulation models to predict femtosecond laser processing of silicon. Optical Materials Express vol. 8, Issue 3. Mar. 1, 2003 [retrieved Dec. 1, 2020]. pp. 648-658.

Notification of Transmittal of the International Search Report and the Written Opinion, International Search Report, and Written Opinion for PCT Application PCT/US2020/047459; dated Jan. 8, 2021; 16 pages.

Bauer et al., "Heat Accumulation in Ultra-Short Pulsed Scanning Laser Ablation of Metals," Optics Express 23(2):1-9 (2015).

Eaton et al., "Heat Accumulation Effects in Femtosecond Laserwritten Waveguides with Variable Repetition Rate," Optics Express 13(12):1-9 (2005).

* cited by examiner

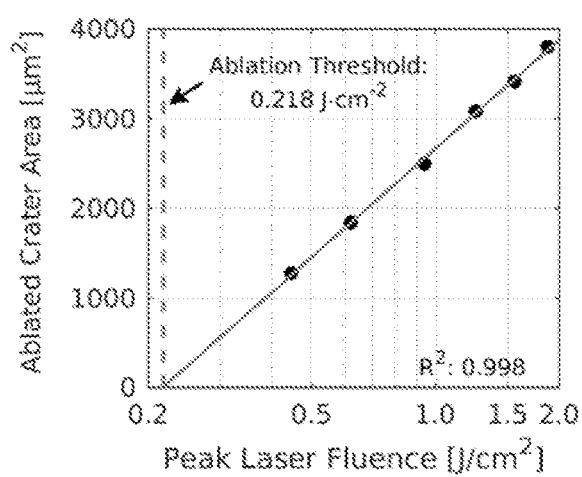 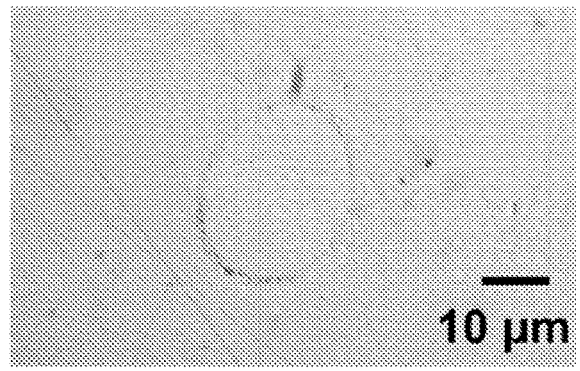
Fig. 6A                                          Fig. 6B

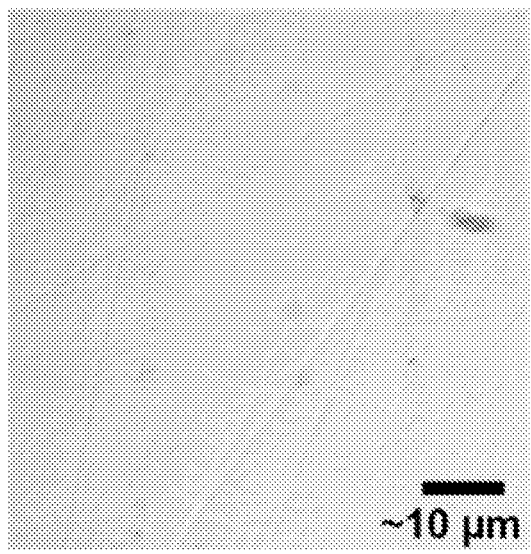
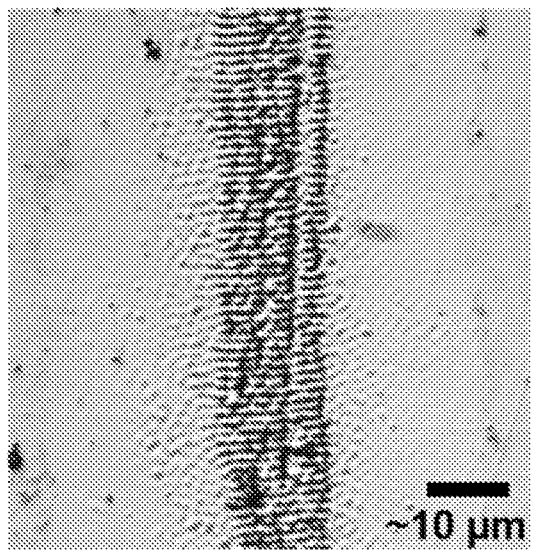
Fig. 7A                                    Fig. 7B

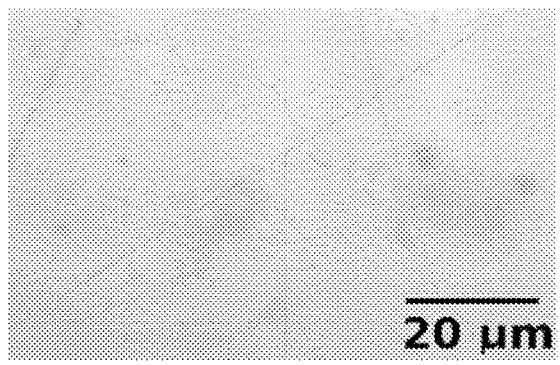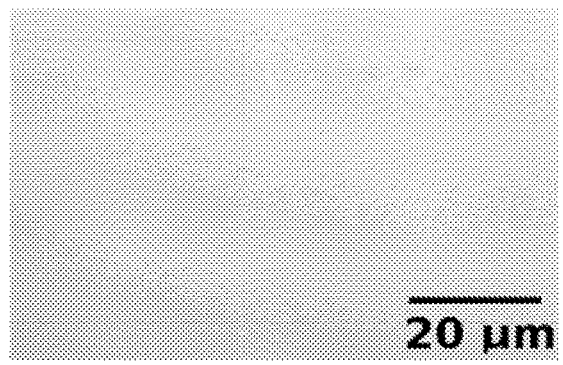
Fig. 8AFig. 8B
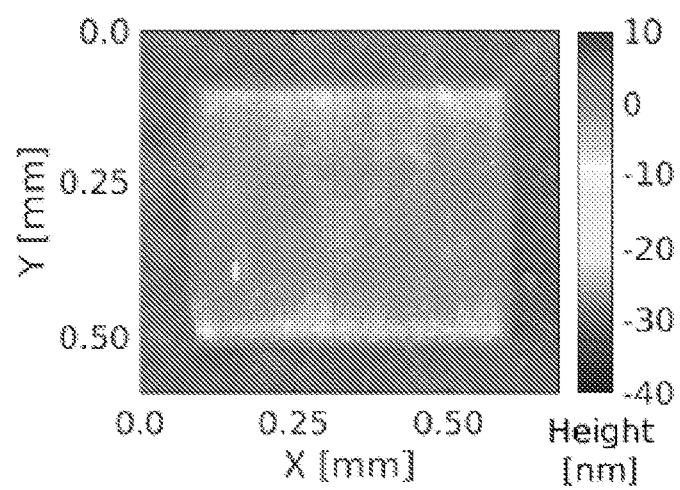
Fig. 8C

METHOD AND SYSTEM FOR ULTRAFAST LASER-BASED MATERIAL REMOVAL, FIGURING AND POLISHING

CROSS REFERENCE

This application claims the benefit of the filing date of U.S. Provisional Patent Application No. 62/889,811, filed Aug. 21, 2019, which is hereby incorporated by reference in its entirety.

This invention was made with government support under grant number IIP-1338877, IIP-1338898, IIP-1822049 and IIP-1822026 awarded by US National Science Foundation (NSF) I/UCRC Center for Freeform Optics. The government has certain rights in the invention.

FIELD

The present disclosure relates to a method and system, including software and physical models, for ultrafast laser-based removal, figuring and polishing of a material and, in particular for ultrafast laser-based removal, figuring and polishing of the surface of a material without leaving tool marks on the material, and/or removing tool marks left by conventional polishing methods.

BACKGROUND

The next generation of imaging systems for applications such as consumer electronics, augmented and virtual reality, and space-based telescopes require advanced optical design strategies to reduce the system footprint and weight while maintaining high optical performance. One such strategy is the integration of freeform optics having complex, rotationally asymmetric surface geometries to condense the task of a system of spherical optics into a single element. To glean the full advantage of these novel optical elements, a standardized process chain for deterministic fabrication is required. This need has provoked the investigation of disruptive tools and techniques to manufacture sophisticated freeform surfaces to optical tolerances. However, it is challenging to manufacture the complex rotationally asymmetric surfaces to optical tolerances.

State-of-the-art ultraprecision forming and finishing tools for freeform optics include deterministic micro-grinding, diamond turning, raster milling, magnetorheological finishing, and ion-beam figuring. These techniques have advanced sub-aperture material removal strategies and flexible tool positioning capabilities which cater to fabricating rotationally asymmetric parts and small, complex surface features. However, the sub-aperture material removal strategies leave behind detrimental mid-spatial frequency (MSF) tool marks on the millimeter scale, and the complexity of sample-tool alignment leads to surface form errors. Contact-based polishing methods also generate significant waste and have long lead times for freeform parts which are disadvantageous for high-volume manufacturing. Therefore, there remains a need for alternative forming, finishing, and post-processing tools for fabricating freeform optics.

Over the last decade, lasers have been readily investigated as a non-contact tool for optical polishing tasks owing to their flexible beam delivery and tunable control of material removal. The predominant polishing strategy utilizes continuous wave and/or micro- and nano-second pulsed lasers to melt and re-flow a layer of the material surface. Continuous-wave $CO_2$ lasers have been used for in-situ healing of laser damage for high-energy laser beam delivery systems and as a smoothing step in a laser-based fabrication chain for freeform optics. Micro- and nano-second pulsed lasers have also been used to polish various metals to nanometer-order roughness. However, melt-based polishing requires precise laser-wavelength/material matching to enable sufficient linear energy absorption to achieve melting. The thermal nature of the laser interaction also causes detrimental structure changes including large sub-surface melt and heat-affected zones, high spatial frequency ripples due to melt front solidification, and form errors due to the flow of molten material. These requirements limit both the versatility and precision of laser micro-polishing, which is currently unsuitable for optic-quality polishing tasks. Currently, the art lacks a high-precision non-contact laser-based polishing methodology and system capable of deterministically figuring, removing defects, and/or smoothing from a material surface without leaving tool marks.

SUMMARY

In accordance with an aspect of the present disclosure, there is provided a system for laser-based removal, figuring and smoothing of a material surface, including:
an ultrafast laser;
a laser beam control module, including a processor for executing machine executable instructions for simulating with a physical model the physical mechanisms of ultrafast laser interaction with a substrate material over a range of laser parameters for a given material, determining from the physical modeling an ablation threshold of the material; determining from the physical modeling whether the underlining physical mechanisms of the laser material interaction include material breakdown induced non-thermal ablation, thermal melting-based material removal, or a combination of the two, determining from the physical modeling a set of optimum laser processing parameters which maximizes non-thermal ablation while eliminating or controlling thermal melting of the material, and determining with a tool path model in combination with the physical model a scanning strategy for a three-dimensional laser scanning path to produce a fluence distribution or energy deposition on the surface of the material in accordance with the optimum laser processing parameters;
a beam delivery system that guides the beam, e.g., with free-space optics or with fibers;
a beam shaping system which generates the spatial, temporal fluence distribution or energy deposition;
a beam scanning system whose timing is synchronized with the laser beam and the positioner of the sample with controlled delays;
a sample fixture and positioning stage; and
optionally, an extraction system that removes the ablated nanoparticles from the surface of the material.

In accordance with another aspect of the present disclosure, there is provided a method for the non-contact laser-based removal, figuring or smoothing of a material surface, including:
collecting thermal and electron properties of a given material;
modeling how absorption of laser energy by the material drives the generation of a dense, hot system of free-carrier electrons which then collides with and transfers heat to the material lattice until the system reaches thermal equilibrium;
simulating how heat accumulates and dissipates over multiple pulses;

predicting material removal mechanisms, comprising material breakdown induced non-thermal ablation, thermal melting-based material removal or a combination of the two;

determining a laser ablation threshold for the material;

modeling temperature evolution at the material surface at a laser fluence near the laser ablation threshold for a range of repetition rates and scanning speeds;

optimizing the repetition rate and scanning speed at the laser fluence to control thermal impact on the surface of the material;

optimizing a scanning strategy comprising the percentage overlap of the line scans to minimize surface scan marks and the number of area scans to determine the desired material removal at a specific location;

determining a beam shape and distribution at the material surface that provides a desired fluence distribution or energy deposition; and scanning a surface of the substrate with an ultrafast laser beam within the determined set of laser parameters, with the beam shape and distribution generated by a beam shaping device and the scanning strategy to remove spatially selective material with a desired thickness, performing at least one of figuring, defect removal, cleaning and smoothing of the material surface without an appearance of tool marks.

In accordance with another aspect of the present disclosure, there is provided a scanning method for eliminating or mitigating ripples caused by the exact overlay of line scans from multiple area scans of a laser scanning method, the method including randomizing a starting position for each area scan following a first of multiple area scans, by spatially dithering a starting position of each line scan in a direction orthogonal to a line scanning direction so that the line scans of multiple area scans do not overlap with each other eliminating ripples otherwise induced by exact overlay of line patterns from multiple area scans.

In accordance with another aspect of the present disclosure, there is provided a method for achieving smooth ultrafast-laser polishing of a material surface, including determining a laser fluence near the ablation threshold of a given material at a given pulse duration and repetition rate; and optimizing a scanning speed and scanning strategy with a line scan overlap between 50% to 85% to minimize heat accumulation at the material surface from scanning with the laser.

These and other aspects of the present disclosure will become apparent upon a review of the following detailed description and the claims appended thereto.

BRIEF DESCRIPTION OF THE DRAWINGS

FIG. 6A is a graph of sensitivity of ablated crater area to single-shot laser fluence and FIG. 6B is an optical microscope image of single-shot processing at a fluence of 0.22 J/cm$^2$ (ablation threshold of germanium);

FIG. 7A is an optical micrograph of line processing using a 1 m/s scan speed and a 250 kHz repetition rate for laser fluence of 0.22 J/cm$^2$ and FIG. 7B for laser fluence of 0.37 J/cm$^2$.

FIG. 8A is an optical micrograph of an unprocessed (control) Ge surface, FIG. 8B is an optical micrograph of a laser-polished Ge surface generated using 20 polishing passes and FIG. 8C shows a surface height map of the 20-pass laser-polished area and the surrounding unprocessed surface;

DETAILED DESCRIPTION

Figure 1:
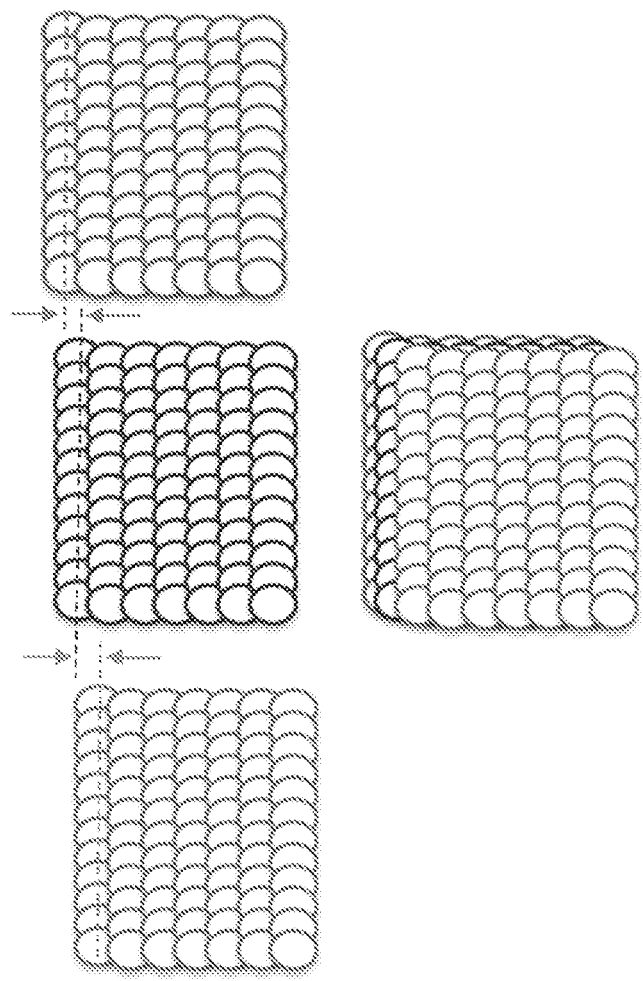
FIG. 1 shows a series (individual and composite) of multiple area scans exhibiting an embodiment of spatial dithering (randomizing) the starting position of each line scan.

The present disclosure relates to a system and method for non-contact figuring, smoothing, material (defect) removing and/or cleaning the surface of a substrate by exposing the surface to a sequence of pulsed laser beams from an ultrafast laser system. An embodiment of the method includes collecting properties of the substrate material as input of a software package that is composed of a set of physical models and a tool path model. The ablation threshold of the material can be determined using the physical models or by experimental procedure. The possible physical mechanism(s) that enable(s) ablation and smoothing is determined, for the selected substrate material. A set of optimum laser parameters that maximize non-thermal ablation while eliminating or controlling thermal melting are determined by the physical model. In an embodiment, a set of laser processing parameters include wavelength, pulse length, fluence (pulse energy/area of the laser spot on surface), repetition rate, and scanning speed. Using the tool path model, the laser scanning path in three dimensions is determined, which includes the three dimensional coordinates of the contours that the laser beam will follow, overlap of the line scans, the overlap of the focused/defocused beam, the starting location of each line scans, and the number of area scans. The laser beam is shaped to produce the model determined fluence distribution on the surface of the material, using either one or multiple focused or defocused beam(s). An ultrafast laser system is operated at a fluence near the model-determined ablation threshold to experimentally fine tune the laser ablation threshold and other model determined processing parameters. The laser beam is shaped to produce a single or multiple beam on the surface of the substrate to improve processing efficiency. Energy density is used as a matrix to normalize the combined effect from a set of laser processing parameters which have different combinations of, for example, pulse energy, focal spot size, scanning speed, repetition rate, overlap of focal spots, line scans and number of area scans. The scanner is controlled to ensure accurate spatial precision and timing delays in laser marking. Material removal depth versus energy density is experimentally determined to remove spatially selective material with the desired thickness, performing figuring/material removal/smoothing of the surface without the appearance of tool marks.

In an embodiment, the method includes the following steps (1) the material properties are collected as input of a software package including a set of physical models and a tool path model. Using the physical models, (2) the ablation threshold of the material can be determined; (3) the possible physical mechanism(s) that enable(s) ablation and smoothing can determined, for the selected material; (4) a set of optimum laser parameters that maximize non-thermal ablation while eliminating or controlling thermal melting can be determined by the model. The set of laser processing parameters include wavelength, pulse length, fluence (pulse energy/area of the laser spot on surface), repetition rate, and scanning speed. (5) Using the tool path model, the laser scanning path in three dimensions can be determined, which includes the three dimensional coordinates of the contours that the laser beam will follow, overlap of the line scans, the overlap of the focused/defocused beam, the starting location of each line scans, and the number of area scans. (5) The laser beam can be shaped to produce the model determined fluence distribution on the surface of the material, using either a focused or a defocused beam. (6) The ultrafast laser system can be operated at a fluence near the model determined ablation threshold (from Step 2) to experimentally fine tune the laser ablation threshold. (7) The laser beam will be shaped to produce a single or multiple beam on the surface of the substrate to improve processing efficiency. (8) Energy density is used as a matrix to normalize the combined effect from a set of laser processing parameters of different combination pulse energy, focal spot size, scanning speed, repetition rate, overlap of focal spots, line scans and number of area scans. (9) The scanner is controlled to ensure accurate spatial precision and timing delays in laser marking. (10) Material removal depth versus energy density can be experimentally determined to remove spatially selective material with the desired thickness, performing figuring/defect removal/smoothing of the surface without appearance of tool marks.

Figure 14:
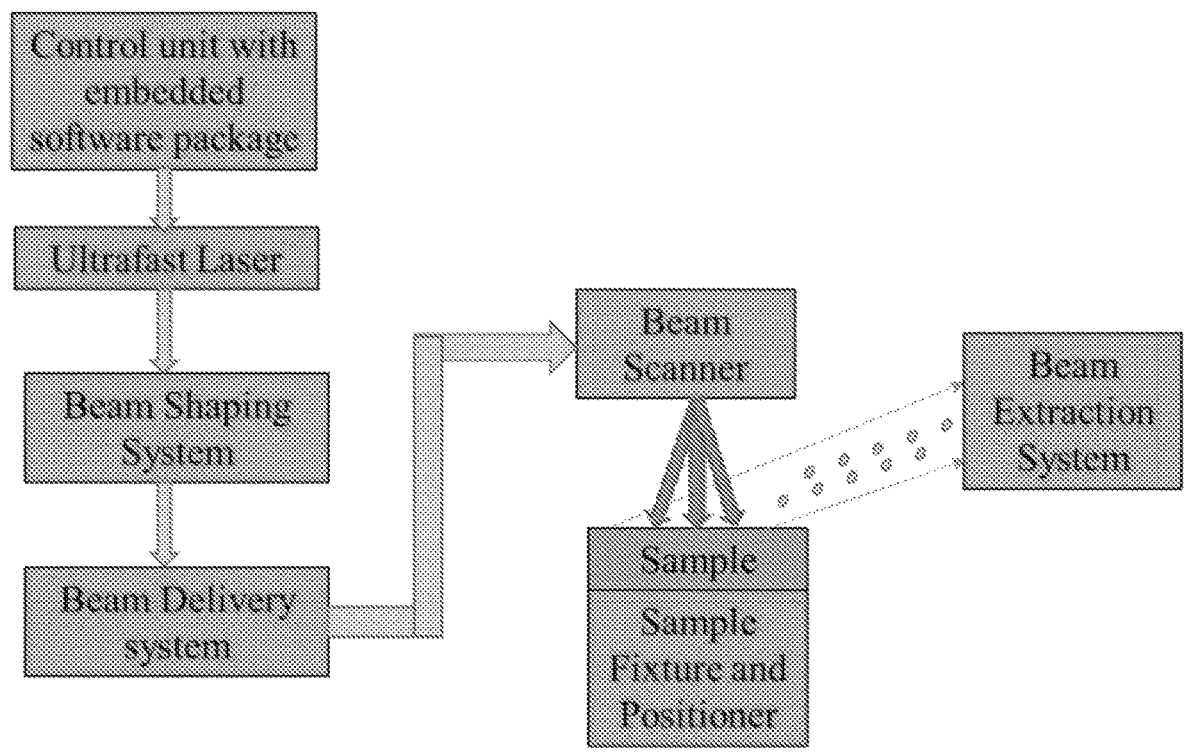
FIG. 14 is a schematic showing an embodiment of a laser-based material surface removal, figuring and smoothing system in accordance with the present disclosure.

FIG. 14 is a schematic showing an embodiment of system components including a control unit, ultrafast laser, beam shaping system, beam delivery system, beam scanner, sample fixture and positioner and beam extraction system in accordance with the present disclosure.

The present method optimizes processing parameters of ultrafast lasers to induce nonthermal ablation/structural changes, where material breakdown is achieved while the thermal impact is minimized and or controlled. When an ultrafast laser is operated at a high repetition rates (e.g., >200 kHz), material can also be removed via heat-accumulation-induced ablation for which solid-liquid-gas phase change occurs. The present methodology also optimizes processing parameters to remove material while avoiding significant thermal melting and large heat-affected zones, as these affect the structural integrity and final roughness of the laser-processed surface. The contributing impact of ablation and temperature rise/melting during laser irradiation is controlled to achieve the desired mix of nonthermal ablation/thermal melting-based material removal conditions for optimum polishing. Physical modeling of the ultrafast laser/material interaction process is conducted to determine the optimum laser parameters for precisely removing material with minimal thermal effects. Depending on the properties of the material, the present ultrafast-laser-based methodology can achieve figuring, material removal, and/or smoothing of the surface via non-thermal ablation alone, thermal melting alone or the combination thereof.

Figure 2A:
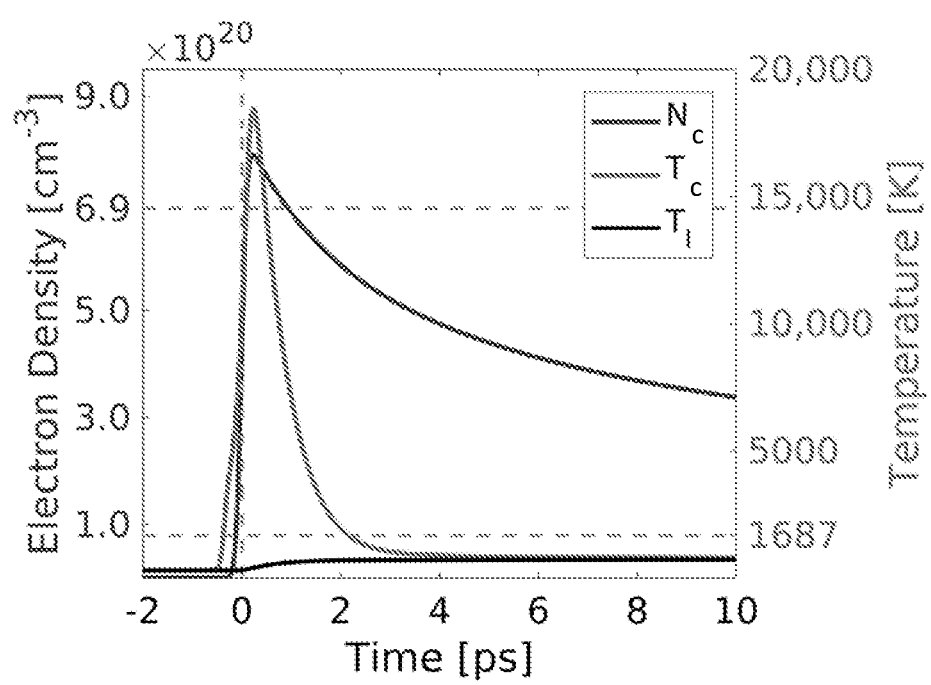
FIG. 2A is a graph showing physical modeling of the physical mechanisms for ablating silicon and FIG. 2B is a graph showing physical modeling of the physical mechanisms for ablating germanium.

In the case that the critical electron density is available for a given material, such as through a literature review, the laser ablation threshold for the material can be determined through physical modeling, as shown for example in FIG. 2A for silicon.

Figure 2B:
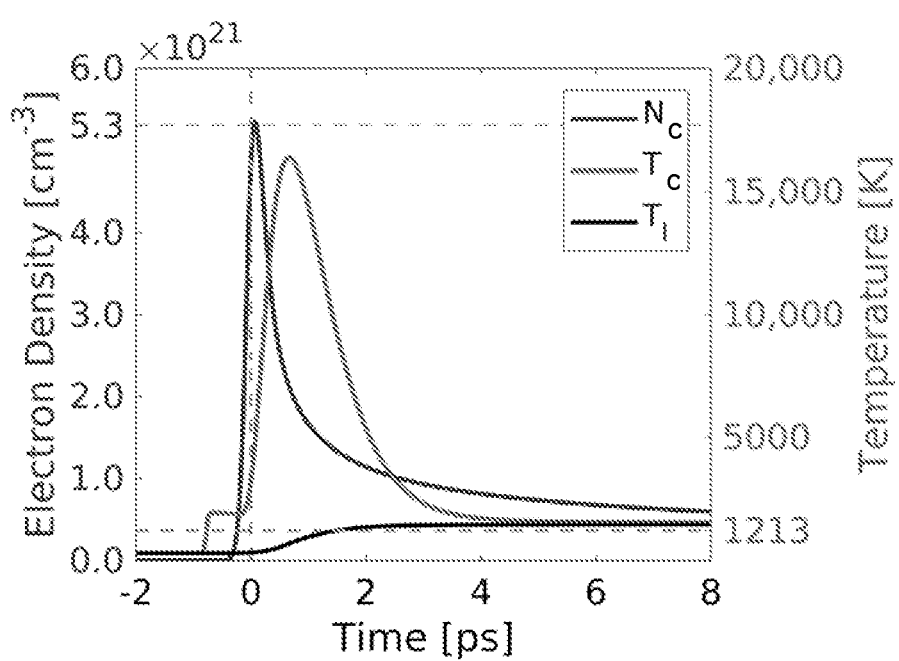

In the case that the critical electron density is not available for a given material, the critical electron density can be determined through physical modeling using an experimentally determined laser ablation threshold, as shown for example in FIG. 2B for germanium.

In either case, the ablation threshold and the critical electron density for a given material can be determined. With this information, it can be further predicted whether non-thermal ablation (when the predicted free electron density exceeds the critical electron density) will occur for any given wavelength, pulse duration, and fluence for a given material. The surface temperature of the material in relation to the melting temperature can also be determined by physical modeling. When the surface temperature exceeds the melting temperature, the time duration that the temperature stays above the melting temperature can be determined, i.e., the extent of the thermal impact. It can be determined what the thermal impact is from single pulse and/or multiple pulses. The laser parameters can be optimized to minimize the thermal impact on the material.

Material description: Suitable substrate materials include for example germanium, silicon, glass, crystal, metal, diamond, sapphire, silicon carbide ceramics and polymer. Suitable materials also include optical and additively manufactured materials.

Laser description: Suitable ultrafast lasers include ultrafast lasers having a pulse duration of less than 50 picoseconds. These include femtosecond and picosecond lasers. Suitable wavelengths of the laser include but are not limited to 248 nm, 355 nm, 385 nm, 515 nm, 527 nm, 532 nm, 615 nm, 620 nm, 775 nm-800 nm, 825 nm, 1030±2 nm, 1045 nm, 1047 nm, 1053 nm, 1060 nm, 1064 nm, 1300 nm, 1550 nm, 1558 nm, and 2400 nm. Suitable repetition rates range from 1 kilohertz to 1 gigahertz, with typical values including 100 kHz and 250 kHz. The laser can be externally triggered and synchronized with a scanner that scans the laser beam to ensure the appropriate laser emission response for a given processing process.

Beam delivery and shaping system description: The laser beam can be a single beam or multiple beams. The spatial and temporal profiles and the relative spatial location and temporal delay among the multiple beams can be shaped by a beam shaping device known in the art, such as a spatial light modulator (SLM). The laser beam can be delivered to the surface of the material for example through free space or via fibers or other manners known in the art. The relative position between the focal spot(s) and the surface can be determined by a model-determined optimum laser fluence on the surface in accordance with the present disclosure, which can be realized by either a focused or defocused beam on the surface of the substrate. In an embodiment, the fluence of the laser beam on the surface of the material is near the ablation threshold of the processed material. The intensity distribution of a laser beam on the surface can hold Gaussian distribution, flat top distribution or user defined other distribution.

Scanning system and scanning strategy description: The scanning system can provide scanning control of the laser beam in three dimensions. The system is synchronized with the laser, and the relative time delay between the laser trigger time and the starting time of the scanner can be adjusted. The scanning strategy includes choosing combinations of scanning speed, overlap of scanning beams along a scan line, overlap of the scanned lines in an area scan (as for example shown in FIG. 1), the starting position of first scan line, number of area scans to achieve the desired ablation depth and surface smoothness, and the line scanning direction in relation to the laser polarization direction.

An embodiment of an optimum scanning strategy includes overlap of scanning beam within each line, overlap of line scans, number of area scans, the line scanning direction in relation to the orientation of the laser polarization, and dithering method to randomize starting position of each line. The overlap of the scanning beam within each scan line can be determined by a combination of laser repetition rate and scanning speed of the beam. A typical repetition rate ranging from 100 kHz to 250 kHz can be used to minimize the thermal impact while maintain scanning speed on the order of 1 m/s. A suitable scanning speed range includes from 0.1 m/s to 4 m/s and can go up as high as 25 m/s or beyond depending upon scanner technology. Suitable overlap of line scans ranges from 50% to 85% of the laser spot diameter. Preferably, the line scanning direction is orthogonal to the laser polarization direction. Preferably, spatial dithering follows a random distribution with the overlap of line scans as the boundary. An optimum scanning strategy is determined via modeling as described herein. The physical models can determine the potential surface temperature and free electron density for a given material, using fluence values near the ablation threshold and the various combinations of scanning parameters within the ranges described herein. A set of scanning parameters with which nonthermal ablation is predicted to occur and thermal impact is minimized with the desired spatial and temporal resolution can be identified as an optimum strategy. Operating the laser at a fluence value near the ablation threshold means a fluence value slightly below, at, or slightly above the ablation threshold.

In an embodiment, the potential periodic imprint, such as ripples, caused by the exact overlays of line scans from multiple area scans can be eliminated or mitigated by spatially dithering for each area scan the starting position of the first line scan in the direction orthogonal to the line scanning direction. FIG. 1 shows an embodiment of dithering wherein the starting position of each line scan in the direction orthogonal to the line scan direction is spatially dithered (randomized) so that the line scans of multiple area scans do not overlap with each other, eliminating potential ripples induced by exact overlay of line patterns from multiple area scans. FIG. 1 shows a sequence of three individual area scans in the left column. The top and bottom figures illustrate two area scans having a random position offset to the left and right relative to the nominal position of the middle scan, respectively. The distance between the lines shown in the sequence represents the dithering amount for the top and bottom area scans, relative to the middle scan whose first line has a nominal position without dithering. The sequence of the three individual area scans is shown in an overlap view as a composite in the right column. The right column figure illustrates that the overlay of the three area scans with spatial dithering breaks the repeat of the periodic pattern shown in the area scan (middle, left column) that has nominal position for the first scan line.

Physical models: Suitable physical models include a Two Temperature Model (TTM), Nonlinear Absorption Model (NAM) and Heat Accumulation Model (HAM), which is an extension of the TTM and NAM models for multi-pulse processing. The TTM or the NAM simulate how absorption of laser energy drives the generation of a dense, hot system of free-carrier electrons which then collides with and transfers heat to the material lattice until the system reaches thermal equilibrium. The TTM considers the energy transfer between electrons and lattices on a pulse scale while NAM consider instantaneous energy transfer from electrons to lattices. TTM is typically used to model semiconductor and metal materials while NAM is typically used to model glass/polymer/ceramics, however, these models can be interchangeable when sufficient material electron properties are known. The models are used to investigate the sensitivity of the free-carrier electron density and the lattice temperature to different laser parameters for a given material. The models can determine possible polishing mechanisms for a specific material, according material properties such as band gap energy, thermal conductivity and heat capacity. Depending upon the type of material and the availability of material properties relating to electrons, either TTM or NAM can be used to (1) determine the physical mechanisms of the laser material interaction; (2) predict laser ablation threshold; (3) predict and control the impact of laser parameters, in particular fluence on nonthermal ablation, the heating and/or temperature evolution of the material, identifying the optimum laser parameters that suppress or induce thermal effect required by the interaction process; and (4) predict and control the impact of the combined laser parameters on heat accumulation, identifying optimum laser processing parameters.

The physical models (e.g., TTM) can be derived from the principals and equations below relating to absorption of laser light (eq. 1); generation of carrier electrons (eq. 2); change of carrier system energy (eq. 3); and transfer of heat to material lattice (eq.4).

$$\frac{\partial I}{\partial z} = -\alpha I - \beta I^2 - \Theta nI \quad \text{Equation 1}$$

$$\frac{\partial n}{\partial t} = \frac{\alpha I}{hv} + \frac{\beta I^2}{2hv} - \gamma n^3 + \theta n - \nabla \cdot \mathcal{J} \quad \text{Equation 2}$$

$$\frac{\partial I}{\partial z} = -\alpha I - \beta I^2 - \Theta nI \quad \text{Equation 3}$$

$$\frac{\partial n}{\partial t} = \frac{\alpha I}{hv} + \frac{\beta I^2}{2hv} - \gamma n^3 + \theta n - \nabla \cdot \mathcal{J} \quad \text{Equation 4}$$

where I is the laser, z is material depth, t is time, n is the number density of the free-carrier electron system; $\alpha$, $\beta$, and $\Theta$ are the respective single-photon, two-photon, and free-carrier absorption cross section coefficients; hv is photon energy [h is Planck constant ($6.63 \times 10^{-34}$ m$^2$ kg/s), and v is fluence of the laser beam], $\gamma$ is the coefficient of Auger recombination, $T_1$ is temperature of the material lattice, $C_1$ is specific heat capacity, $\kappa_1$ is thermal conductivity, U is energy density in the electron-hole pairs, $\overline{W}$ is current, $T_e$ is carrier energy temperature, $C_{e-h}$ is heat capacity specific to electron-hole pairs, and $\tau_e$ is electron relaxation time.

The TTM/NAM is used to investigate the sensitivity of the free-carrier electron density and the lattice temperature to different laser parameters. Simulating the free carrier density allows prediction of material breakdown and simulating the lattice temperature rise can predict the onset of thermal melting during processing. These two predictions allow one to (1) determine whether the underlining physical mechanisms of the laser/material interaction is (a) material breakdown induced non-thermal ablation, or (b) thermal melting-based material removal, or (c) combination of the two ((a) and (b)) and (2) predict the laser ablation threshold for a given material.

FIG. 2A shows that for silicon, when operating the laser at a fluence near the ablation threshold, the free electron density exceeds the threshold value for material breakdown, but the maximum temperature is less than the melting temperature of silicon. This indicates that the physical mechanism for ablating silicon at the laser ablation threshold is non-thermal ablation only.

FIG. 2B shows that for germanium, when operating the laser at a fluence near the ablation threshold, the free electron density exceeds the threshold value for material breakdown while the maximum surface temperature is slightly above the melting temperature of germanium. The physical mechanism for material removal when operating the laser at a fluence near the ablation threshold is the combination of non-thermal ablation and thermal melting-based material removal.

For example, for germanium having a laser fluence of 0.22 J/cm$^{-2}$, processing conditions include a laser fluence near the ablation threshold of 0.2 J/cm$^{-2}$ at 1030 nm, 300 fs, scanning speed of 1 m/s, repetition rate of 250 kHz, 75% of line scan overlap, a smooth laser polished is achieved and the thickness of the material to be removed is further determined by the number of area scans per the determined energy density.

The TTM or NAM can be used to predict the laser ablation threshold for a given material via simulating the impact of laser fluence on the achieved maximum free-carrier number density. The corresponding fluence value at which the free electron density exceeds the threshold value for material breakdown is determined as the ablation threshold. This method provides an alternative to the conventional process of experiment-based trial and error for determining the ablation threshold.

Figure 3A:
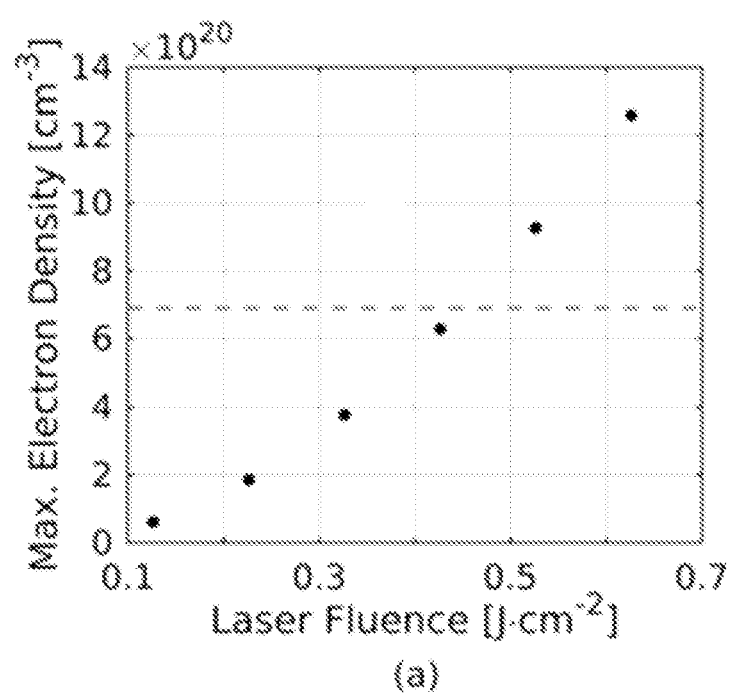
FIG. 3A is a graph showing the determined ablation threshold for silicon through physical modeling and FIG. 3B is a graph experimentally validating the modeling determined ablation threshold.
Figure 3B:
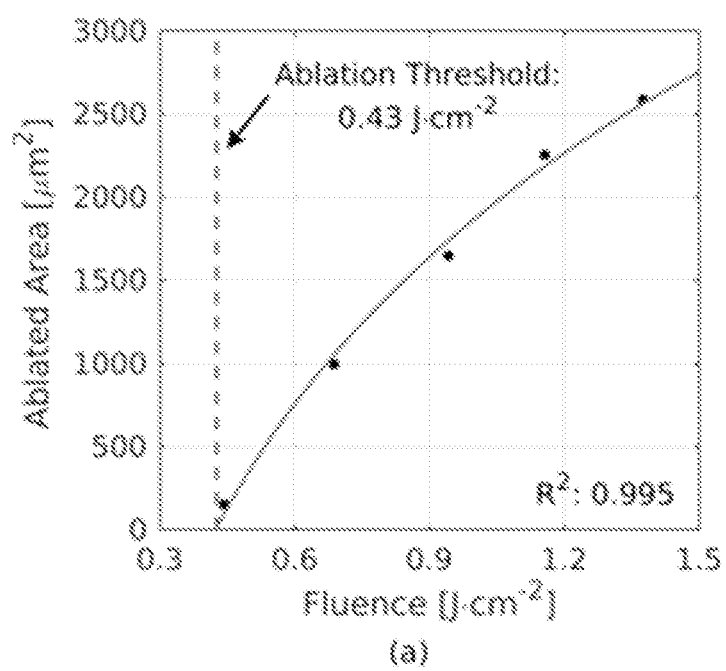

As an example, FIG. 3A shows that the maximum free-carrier number density increases with increasing laser fluence. The model determined fluence threshold for achieving ablation is ~0.45 J/cm$^2$ at which the carrier density is equal to the critical value of $6.9 \times 10^{20}$ cm$^{-3}$. The model determined ablation threshold for silicon is experimentally validated as shown in FIG. 3B.

The TTM/NAM can be used to predict/control the impact of laser parameters, in particular fluence, on the heating and/or temperature evolution of the material, identifying the optimum laser parameters that suppress or induce the thermal effect required by the interaction process.

The TTM/NAM and HAM can be used to predict and control the impact of the combined laser parameters on non-thermal ablation and heat accumulation, thus identifying optimum laser processing parameters.

Operational laser parameters include wavelength, pulse duration, fluence at the location of the surface interacting with the laser beam, laser repetition rate, scanning speed of laser beam relative to the material, overlap between the line scans, and polarization of the laser beam. An example of a suitable set of operating parameters for smoothing a germanium surface is 1030 nm wavelength, 300 fs pulse duration, 0.22 J/cm$^2$, 250 kHz repetition rate, 1 m/s scanning speed, 75% overlap between scan lines, and the direction of line scans is orthogonal to the orientation of the laser polarization. Preferably with respect to smoothing quality, laser polarization is orthogonal to the direction of line scans compared to a polarization direction that is along the line scan direction.

Smoothness, cleaning/defect material removal and figuring: The surface of the material can be smoothed to a surface roughness of less than 10 nanometers or a roughness that is larger than 10 nanometers when desired. The surface can be flat, curved, or freeform. The system and method enable layer by layer removal of the substrate surface with nanometer precision control achieving figuring, smoothing, and cleaning/defect removal. The system and method have been demonstrated for a material removal depth increasing from 4 nm to approximately 30 nm when increasing the number of polishing passes from 15 to 100. The optic-quality surface with ≤1.5 nm RMS roughness is consistently maintained for various material removal depths (FIG. 10 A). The material removal depth can be further increased to micro level via using larger numbers of scans and multi beam processing.

An embodiment of the system includes an ultrafast laser; a laser beam control module; a beam delivery system; a beam shaping system providing the desired fluence distribution or energy deposition; a scanning system whose timing is synchronized with the laser beam with controlled delays; and a sample fixture and positioning stage.

In an embodiment, the laser beam control module includes a processor which executes machine executable instructions for simulating with physical model(s) the physical mechanisms of ultrafast laser interaction with a given substrate material over a range of laser parameters, determining from physical modeling or experimentally an ablation threshold of the material; determining from physical modeling whether the underlining physical mechanisms of the laser material interaction are material breakdown induced non-thermal ablation, thermal melting-based material removal, or a combination thereof, determining from physical modeling a set of optimum laser processing parameters which maximizes the non-thermal ablation while eliminating or controlling thermal melting of the material, and determining with a tool path model in combination with a physical model a scanning strategy for a three-dimensional laser scanning path to produce a fluence distribution or energy deposition on the surface of the material in accordance with the optimum laser processing parameters.

Sample fixturing and positioning stage description: The laser polishing system can be equipped with a sample fixturing and positioning stage known in the art to ensure accurate and repeatable alignment of various samples to the laser system.

Extraction subsystem description: the laser polishing system can be equipped with an extraction system known in the art that removes the ablated nanoparticles from the surface.

The following publications are incorporated herein by reference in their entireties: L. L. Taylor, J. Xu, M. Pomerantz, T. R. Smith, J. C. Lambropoulos, and J. Qiao, "Femtosecond Laser Polishing of Germanium towards Freeform Fabrication [Invited]," Optical Materials Express 9 (11), 4165-4177 (2019); K. Mishchik, G. Bonamis, J. Qiao, J. Lopez, E. Audouard, E. Mottay, C. Hönninger, and I. Manek-Hönninger, "High-efficiency femtosecond ablation of silicon with GHz repetition rate laser source," Opt. Lett., 44, 2193-2196 (2019); L. Taylor, R. Scott, and J. Qiao, "Predicting Femtosecond Laser Processing of Silicon via Integrating Thermal and Two-Temperature Models," Optics Materials Express, Optical Materials Express 8 (3) 648-658 (2018); and L. Taylor, Jun Qiao, and Jie Qiao, "Optimization of femtosecond laser processing of silicon via numerical modeling," Optics Materials Express, 6 (9), 2745-2758 (2016).

To address the need for disruptive, high-precision sub-aperture forming and finishing techniques for freeform optics, the present disclosure provides an alternative, non-contact material removal, figuring and polishing methodology and system using an ultrafast laser. The ultrafast-laser-based polishing technique is capable of high-precision material removal while maintaining optical surface quality. The polishing methodology opens a viable path for sub-aperture, optic quality finishing of optical materials with the capability to scale up to address complex polishing tasks towards freeform fabrication. The present disclosure enables deterministic, high-speed, high-quality material removing, figuring and polishing with negligible tool/thermal artifacts, without the need for time-consuming, iterative experiments.

In comparison to conventional grinding/polishing techniques, the present ultrafast-laser-based polishing is a green manufacturing technique producing minimal waste (i.e., no slurries, chemicals, water, purge gasses, etc. are needed). The precise, localized material removal achieved is transformative for processing small, freeform optical features which currently cannot be accessed by sub-aperture material-removal tools. Mid-spatial-frequency ripples left by machine tools can be mitigated as a result of the size of the laser beam. High powers/scanning speeds/repetition rates offer increased processing speeds which rival current conventional polishing techniques.

An important aspect of the disclosure relates to two components which are inter-linked via feedback loops: (1) fundamental, theoretical modeling to investigate the ultrafast laser/material interaction mechanism and the impact of laser parameters, and (2) experimental implementation of ultrafast laser-based processing of materials. The developed laser/material interaction process directly enables, high-precision polishing of, for example germanium, using ultrafast lasers, i.e., selectively removing material while maintaining an optic-quality surface. The method can be extended to other optical materials and additively manufactured materials for wide application in optics and photonics fabrication applications.

Important aspects/attributes of this disclosure include: an ultrafast laser polishing system developed for achieving material removal based on material breakdown and/or thermally controlled melting. A laser scanning strategy established to achieve ablation and avoid the onset of undesired thermal effects by controlling the combined impact of laser parameters. A Two-Temperature Model/Nonlinear Absorption Model and a Heat Accumulation Model used to investigate the femtosecond laser/material interaction mechanism. Controllable laser polishing is achieved using a set of model-determined operational laser parameters. The potential underlying mechanism for ultrafast laser-based polishing of a given material is determined via laser/material interaction modeling.

Ultrafast lasers enable precise, spatially localized ablation-based material removal with minimal thermal impact on various materials having different optical properties. This disclosure exploits the unprecedented material removal capabilities offered by these specialized lasers to develop a space-selective, high-precision material removal strategy which maintains optic-quality surface roughness.

This disclosure has several important uses (also applicable for commercialization): Standalone tool for final-finishing and/or form correction for high-precision and freeform optics manufacturing. This is important at the current time, as the field of freeform optics manufacturing is in dire need of a new tool for high-precision material removal which can offer the following attributes: (1) high precision for complex/small surface geometries and both weak and strong surface departures, (2) ability to perform polishing without and/or remove existing fabrication-induced tool marks from the optic surface, (3) capability to process a variety of different crystalline and amorphous materials and also brittle materials, (4) reduction of polishing cost, waste, and lead-time. Other uses include integration into an ultraprecision machine tool or an existing optics grinding/polishing process chain (e.g., diamond turning, magnetorheological finishing). Integration with other high-power lasers to develop a full, laser-based optic manufacturing station (e.g., using $CO_2$ and/or nanosecond Nd:YAG lasers to shape/initially polish an optic preform and use the described technology for final, high-precision finishing of the part). Integration with laser-based additive manufacturing machines for inter-layer smoothing/densification and final surface polishing. Integration with laser structuring and laser welding to realize integrated optics/micro-optics/photonics.

This disclosure provides a fundamental understanding of how to precisely balance the contributing laser-interaction phenomena to control material breakdown and material phase change to achieve polishing. This balance can be revealed by using both physical modeling and experiments to develop a feedback loop to drive the selection of laser parameters to effectively control the material removal mechanism to achieve controllable and repeatable polishing. The ultrafast laser-based polishing is achieved though the high-precision thermal controllability via tuning the spatial and temporal energy deposition, in combination with material breakdown. The process is adaptable to a given material. The present disclosure takes advantage of the significance of the fine thermal control ability of femtosecond lasers in methodologies that heretofore have used continuous wave or nanosecond lasers for purely melting induced polishing. Femtosecond lasers were used to drive non-thermal ablation-based polishing while there was a lack of methodology to control the often-accompanying thermal effect with high spatial and temporal resolution.

This disclosure can directly compete with conventional final-finishing techniques for optical fabrication, such as Ion-Beam Figuring, and offer a "green" technology for optical polishing. The scale-up of material removal can allow the technique to compete with other ultraprecision tools for optical fabrication. The refined processing capability offered can eliminate the need for melt-based laser polishing with pulsed and/or CW lasers, which has lower precision and limited tunability for addressing different materials and complex surface geometries than the present methodology.

The disclosure will be further illustrated with reference to the following specific examples. It is understood that these examples are given by way of illustration and are not meant to limit the disclosure or the claims to follow.

Example 1

To determine the possible physical mechanisms for ultrafast laser interaction with both silicon and germanium materials, both free electron density and surface temperature are predicted by physical modeling at a fluence value near the ablation threshold of the material.

FIG. 2A shows that for silicon, when operating the laser at a fluence value near the ablation threshold, the free electron density exceeds the threshold value for material breakdown, but the maximum temperature is less than the melting temperature of silicon. The analysis indicates that the physical mechanism for ablating silicon at the laser ablation threshold is non-thermal ablation only. More specifically, the TTM predicted that, for silicon, when the laser fluence value is at 0.43 J/cm$^2$ (i.e., the silicon ablation threshold) the electron number density increases to $9.3 \times 10^{20}$, exceeding the threshold for silicon breakdown ($6.9 \times 10^{20}$ cm$^{-3}$), predicting the occurrence of non-thermal ablation. The TTM predicts surface temperatures not to exceed the silicon melting temperature of 1687 K, therefore no thermal melting occurs in the ablation process.

FIG. 2B shows that for germanium, when operating the laser at a fluence value near the ablation threshold, the free electron density exceeds the threshold value for material breakdown while the maximum surface temperature is slightly above the melting temperature of germanium. This analysis indicates that the physical mechanism for material removal when operating the laser at a fluence value near the ablation threshold is the combination of non-thermal ablation and thermal melting-based material removal. More specifically, the TTM predicted that, for germanium, when the laser fluence value is at 0.22 J/cm$^2$ (i.e., the germanium ablation threshold) the electron number density increases from an initial value of $10^{13}$ cm$^{-3}$ to a value on the order of $10^{21}$ cm$^{-3}$ in less than one picosecond after the arrival of the peak intensity. This density is characteristic of the onset of material breakdown in semiconductors, indicating the potential onset of ablation. The TTM result predicts surface temperatures exceed the Ge melting temperature of 1213 K, leading to the onset of melting, confined to nanometer-order depth.

Example 2

In this example, the silicon laser ablation threshold is determined by the TTM via simulating the impact of laser fluence on the achieved maximum free-carrier number density. The corresponding fluence value at which the free electron density exceeds the threshold value for material break down is determined as the ablation threshold. This eliminates the need for experiment-based trial and error to determine the ablation threshold.

FIG. 3A is a graph of TTM-simulated maximum electron number density versus laser fluence for laser-silicon interaction (300 fs pulse width, 1030 nm wavelength), which shows that the maximum free-carrier number density increases with increasing laser fluence. The dashed line marks the critical density above which ablation occurs ($6.9 \times 10^{20}$ cm$^{-3}$). The model determined fluence threshold for achieving ablation is ~0.45 J/cm$^2$ at which the carrier density is equal to the critical value of $6.9 \times 10^{20}$ cm$^{-3}$.

The model-determined ablation threshold value for silicon shown in FIG. 3A is experimentally validated, as shown in FIG. 3B, which is a graph of ablated crater area on silicon versus laser pulse fluence. The ablation threshold was experimentally determined to be 0.43 J/cm$^2$, corresponding to the x-intercept of the regression curve.

Example 3

TTM/NAM is used to predict/control the impact of laser parameters, to predict fluence on the heating and/or temperature evolution of the material, identifying the optimum laser parameters that suppress or induce thermal effect required by the interaction process.

Figures 4A, 4B, 4C:
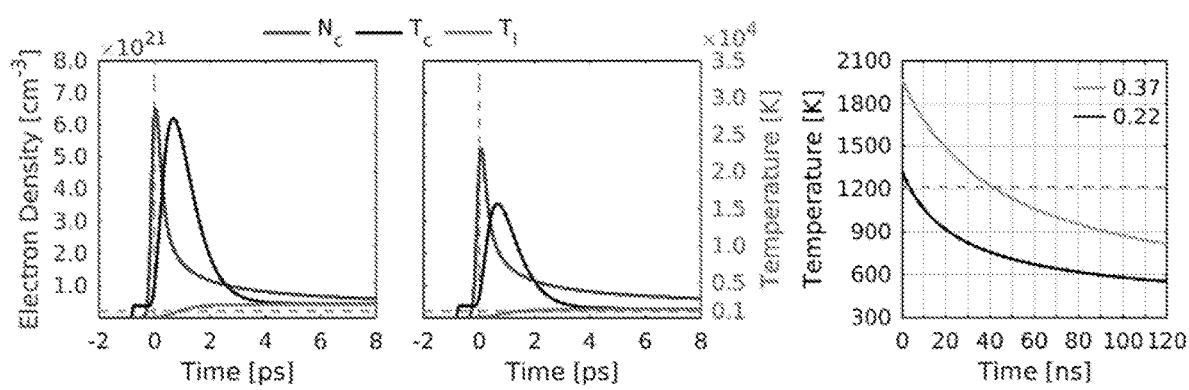
FIG. 4A is a graph showing Two Temperature Model (TTM)-simulated number density of free-carrier electrons (Nc), carrier-system temperature (Tc), and lattice temperature (Tl) at the location of peak intensity for incident-pulse fluences of 0.37 J/cm$^2$, FIG. 4B a graph of 0.22 J/cm$^2$.
FIG. 4C is a graph comparing heat diffusion behavior on the nanosecond timescale post electron/lattice temperature equilibration for the fluences shown in FIGS. 4A and 4B.

FIGS. 4A-4B show the TTM-simulated number density of free-carrier electrons ($N_c$), carrier-system temperature ($T_c$), and lattice temperature ($T_1$) at the location of peak intensity for incident-pulse fluences of (FIG. 4A) 0.37 J/cm$^2$ and (FIG. 4B) 0.22 J/cm$^2$ for a single pulse. FIGS. 4A and 4B compare the TTM results at the material surface and in the spatial center of the incident Gaussian pulse for the two different peak fluences shown. Times are relative to the arrival of the peak pulse intensity at 0 ps. This density is characteristic of the onset of material breakdown in semiconductors, indicating the potential onset of ablation for both cases. The generation of free-carrier electrons causes the electron-system temperature to rise to $2.9 \times 10^4$ K for a fluence of 0.37 J/cm$^2$ and to $1.6 \times 10^4$ K for a fluence of 0.22 J/cm$^2$. The higher electron temperature allows stronger coupling of thermal energy to the material lattice, causing the lattice temperature to rise to nearly 2100 K for the higher fluence, and ~1400 K for the lower fluence. Both predicted surface temperatures exceed the Ge melting temperature of 1213 K. For the lower fluence case, only the onset of melting, confined to nanometer-order depth, is predicted based on the amount of energy supplied to the simulated lattice voxel.

FIG. 4C shows the dissipation of surface temperature following laser irradiation and electron/lattice temperature equilibration. In all plots, the dashed horizontal line corresponds to the Ge melting point at 1213 K. FIG. 4C compares heat diffusion behavior on the nanosecond timescale post electron/lattice temperature equilibration. The surface temperature induced by the 0.22 J/cm$^2$ fluence is predicted to dissipate to below the melting point an order of magnitude faster than for 0.37 J/cm$^2$ (4 ns vs. 40 ns). This indicates that reducing laser fluence can minimize the time over which detrimental thermal melting may occur. Therefore, a fluence near 0.22 J/cm$^2$ is expected to induce ablation while controlling the extent of thermal effects. FIG. 4C shows that the time for the material (germanium) to stay above the melting temperature can be controlled within nanosecond precision, which ensures the thermal impact will only occur on a single atom layer.

Example 4

Figure 5A:
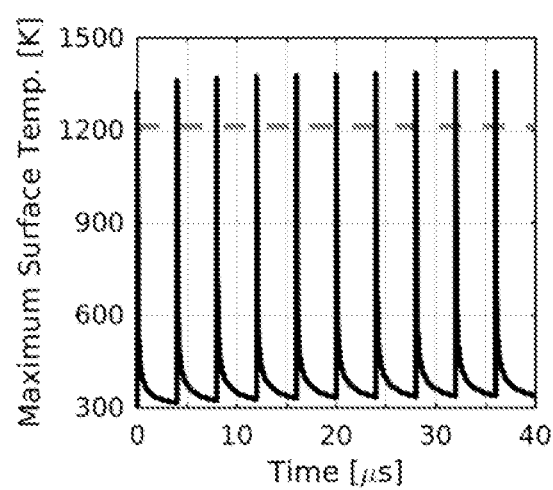
FIG. 5A is a graph of modeled maximum surface temperature corresponding to the location of peak fluence of the immediate-past pulse and FIG. 5B is a graph of modeled predicted base surface temperature achieved prior to the next laser pulse.
Figure 5B:
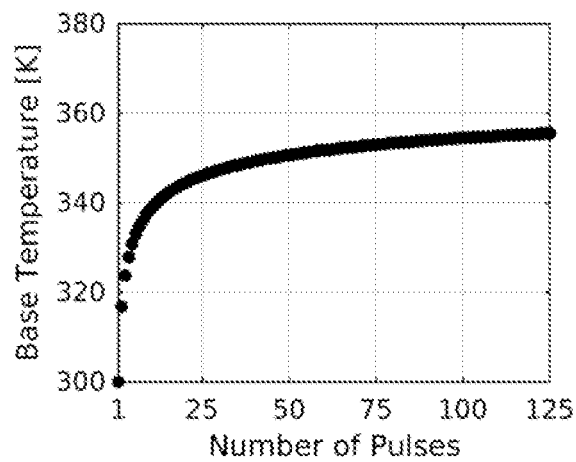

To predict heat accumulation, the TTM/NAM was extended to three spatial dimensions to simulate multi-pulse laser-material interaction for area processing. FIGS. 5A-5B predicted surface temperature evolution due to femtosecond laser interaction using the initially determined set of laser parameters. The TTM was used to evaluate and control heat accumulation and the onset of thermal effects during multipulse processing/polishing, using a fluence of 0.22 J/cm$^2$, a scanning speed of 1 m/s, and a repetition rate of 250 kHz. FIG. 5A shows that the maximum surface temperature corresponds to the location of peak fluence of the immediate-past pulse. FIG. 5A shows that for each laser pulse, the surface temperature rises and then dissipates due to heat diffusion in the time between laser pulses. As more pulses are deposited, heat continues to accumulate until the thermal energy deposited by each laser pulse and the amount of heat dissipated between pulses reach equilibrium, controlled by the Ge thermal properties (specific heat capacity, thermal conductivity).

FIG. 5B shows the predicted base surface temperature achieved prior to the next laser pulse for processing with 125 laser pulses, insuring that after multiple pulse material is not melting. FIG. 5B shows that the base temperature achieved immediately prior to the next laser pulse begins to settle after 25 pulses at a temperature of 345 K. Between 25 and 125 pulses, the base temperature is predicted to rise by only ten Kelvin to a value of 355 K. This demonstrates the capability for the selected laser parameters to produce controlled thermal processing conditions with minimal heat accumulation while producing a pulse overlap in the regime for uniform processing. Therefore, the combination of a 0.22 J/cm$^2$ laser fluence, a 250 kHz repetition rate, and a 1 m/s scan speed is shown as a suitable set of laser parameters for polishing.

Example 5

Point and line processing experiments were carried out to evaluate the TTM-predicted laser parameters for femtosecond laser polishing of Ge. Experiments were performed on Ge substrates with <111> crystal orientation and ~1 nm root mean square (RMS) surface roughness, cleaned with isopropanol and/or methanol before irradiation. Substrates were processed using a 300 fs, 1030 nm Ytterbium fiber laser (Satsuma HP3, Amplitude Systémes). Beam attenuation, scanning, and focusing were controlled using integrated beam control and scanning hardware (LS-Shape and LS-Scan, Lasea). The 1/e$^2$ radius of the laser focal spot is 30 μm.

FIG. 6A shows an experimental sensitivity study of laser fluence on ablation carried out using single-shot laser pulses. FIG. 6A shows the impact of laser fluence on the resulting area of ablation craters as measured by a Zygo NewView interferometric microscope. The relationship between the crater area A, and the laser fluence $F_l$, is defined as $A=(\pi \cdot w_o^2/2)\cdot \ln(F_l/F_{th})$, where $F_{th}$ is the ablation threshold fluence and $w_o$ is the 1/e$^2$ radius of the laser beam. Fitting this relationship to the experimental data yielded an ablation threshold of approximately 0.2 J/cm$^2$ for Ge. FIG. 6B is an optical microscope image showing that single-shot processing at a fluence of 0.22 J/cm$^2$, near the ablation threshold, modifies the surface region without generating rough central features like melt-induced ripples or nucleated gas bubbles. This confirms the TTM-prediction that the 0.22 J/cm$^2$ fluence is capable of ablation-based material removal.

Line-configuration processing was also carried out to examine the combined effectiveness of the TTM-investigated fluence, repetition rate, and scan speed towards polishing Ge. The processed region corresponds to the ~30-50 μm wide bright track and the structures therein. FIG. 7A is an optical micrograph of line processing using a 1 m/s scan speed and a 250 kHz repetition rate for a laser fluence of 0.22 J/cm$^2$. FIG. 7A shows that the parameters generate a uniformly colored processing track with potential surface smoothing, evidenced by "blurring" of the scratches which passed through the processing track. FIG. 7B is an optical micrograph of line processing using a 1 m/s scan speed and a 250 kHz repetition rate for a laser fluence of 0.37 J/cm$^2$. FIG. 7B shows that using a higher fluence of 0.37 J/cm$^2$ for the same repetition rate and scan speed produces rough structures in the center of the processed track. The structures have periodicity on the order of the laser wavelength resulting from interference between the incident electric field and the dense ionic plasma generated by the laser pulses. They are also potentially exacerbated by the thermal impact of processing at higher fluences, indicated by the model-predicted lattice temperature of 2100 K (significantly above the Ge melting point of 1213 K) for processing with a fluence of 0.37 J/cm$^2$.

According to the modeling results shown in FIG. 4B and FIG. 4C and the experimentally determined Ge ablation threshold, ablation and the onset of melting will most likely occur simultaneously during laser polishing of Ge. Thus, the aim is to achieve as close to a nonthermal ablation state as possible to minimize thermal effects and heat-affected zones. The experimental results for point and line processing guided by the TTM model prediction confirm that selecting a laser fluence near the ablation threshold and a repetition rate and scanning speed to minimize heat accumulation is a strategy towards achieving smooth femtosecond laser polishing.

Example 6

Femtosecond laser polishing experiments were carried out using the experimentally validated set of laser parameters for smooth processing shown in FIG. 7A. A strategy to generate overlapping lines of processing was devised to polish a region of the Ge surface (~0.5 mm×0.5 mm). Lines were marked unidirectionally with line overlap initially set to 75% of the laser focal spot diameter to maintain processing efficiency. A completed scan over the defined polishing area is referred to as a "polishing pass".

FIG. 8A is an optical micrograph of an unprocessed (control) Ge surface compared to an optical micrograph of a laser-polished Ge surface generated using 20 polishing passes shown in FIG. 8B. The laser parameters used include a laser fluence of 0.22 J/cm$^2$, line overlap of 75%, 250 kHz repetition rate, scanning speed of 1 m/s, number of area scans of 1200. The representative optical micrographs in FIGS. 8A and 8B show that the control surface contains defects including scratches and discoloration which are not evident in the laser-polished surface.

Figures 9A, 9B, 9C:
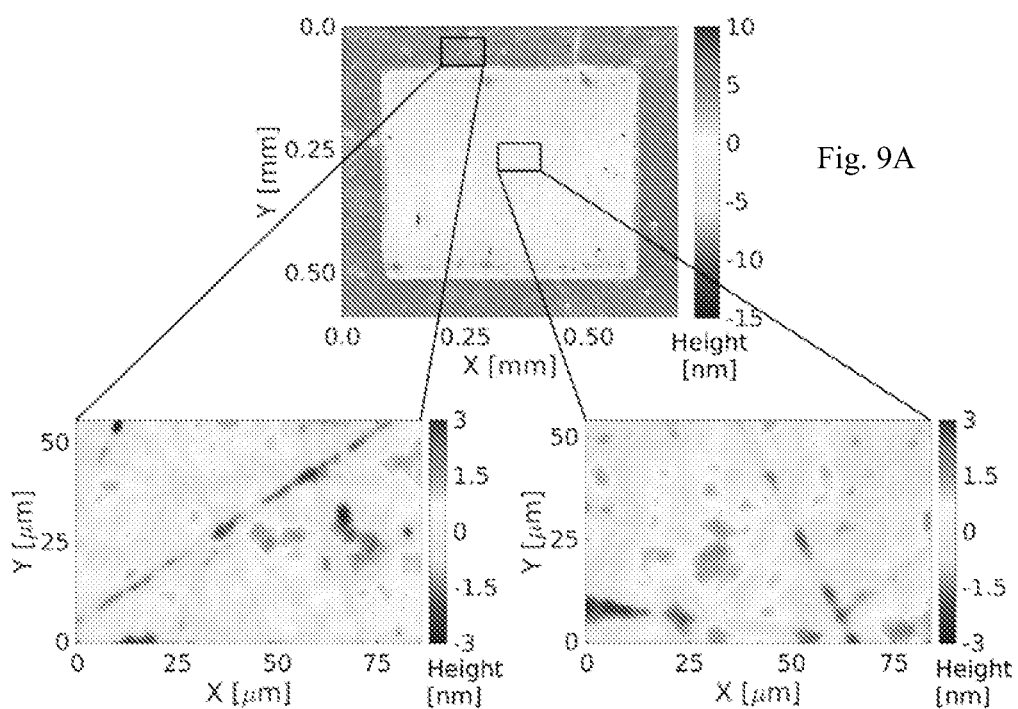
FIG. 9A shows a surface height map of a 20-pass laser-polished area and the surrounding unprocessed surface.
FIG. 9B shows a zoomed-in surface profile of an unprocessed area.
FIG. 9C shows a zoomed-in surface profile of a laser-polished area.

FIG. 9A shows a full-area Ge polishing surface height map of a 20-pass laser-polished area and the surrounding unprocessed surface (measured using a Zygo NewView). The depth of material removal in the polished area is 6 nm. The slight deepening of the removal at the top and bottom edges of the polished region follows from increased laser dwell time due to scanning acceleration and the slight striation in the area follows from the initial line overlap selection, both of which are undergoing correction. The average RMS roughness in the center of the laser-polished area is 0.826±0.102 nm, and that of the surrounding unprocessed area is 0.824±0.185 nm (averages calculated over five, 150 μm×150 μm regions). Representative zoomed-in surface profiles of unprocessed and laser-polished areas are shown in FIGS. 9B and 9C, corresponding to the locations of the images in FIGS. 8A and 8B. The femtosecond-laser-polished area maintained single-digit nanometer surface roughness quality, e.g., 0.72 nm RMS in comparison to 0.78 nm in the unprocessed region.

The results in FIGS. 8A-8B and FIGS. 9A-9C demonstrate that the devised laser polishing strategy effectively removes surface defects while maintaining sub-nanometer optic-quality surface roughness, revealing the capability of femtosecond laser polishing for high-precision material removal tasks.

The controllability of material removal by femtosecond laser polishing was investigated by varying the number of polishing passes and/or the overlap of the scanned lines provided by a various combination of laser parameters of laser pulse energy, scanning speed and repetition rate.

Figure 10A:
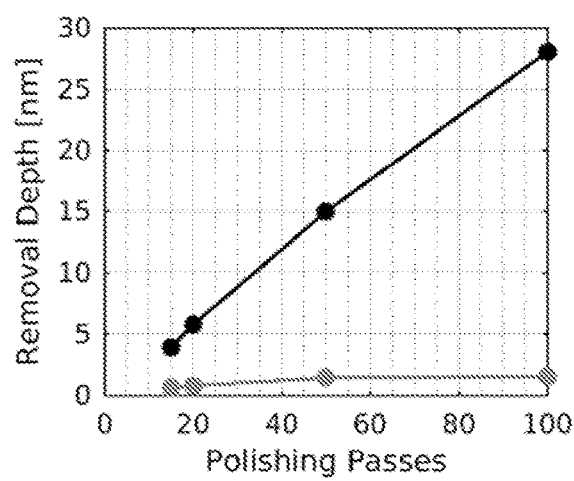
FIG. 10A is a graph showing the impact of the number of polishing passes on material removal depth (black line) and the resulting RMS surface roughness (grey line) and FIG. 10B is a graph showing the material removal depth verses total deposited energy density.
Figure 10B:
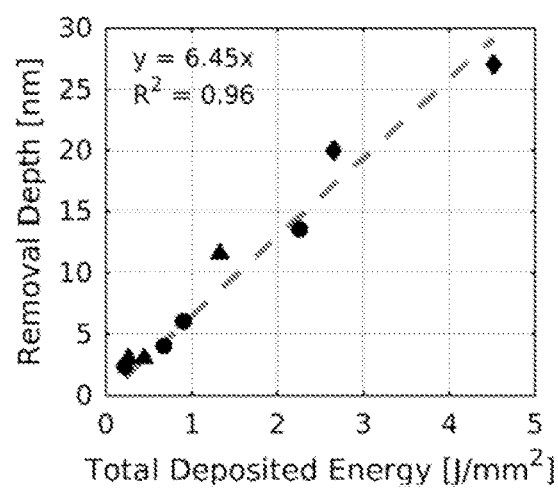

FIG. 10A shows the impact of the number of polishing passes on material removal depth (black) and the resulting RMS surface roughness (gray). FIG. 10A shows that the material removal depth increases from 4 nm to approximately 30 nm when increasing the number of polishing passes from 15 to 100. The optic-quality surface with ≤1.5 nm RMS roughness is consistently maintained for various material removal depth. FIG. 10B shows the material removal depth versus total deposited energy varied by polishing with: (▲) 10 passes/scan-line overlap of ~60 to 90% of the laser spot diameter, (◆) 100 passes/scan-line overlap of ~60 to 75%, and (●) 5 to 20 passes/75% scan-line overlap. FIG. 10B shows that material removal depth linearly follows the total deposited laser energy density resulting from various combinations of line overlaps and numbers of polishing passes. This demonstrates that the deposited energy per area can be used as a metric by which laser parameter combinations can be determined to maximize the processing efficiency, accommodate larger-scale polishing tasks and rougher surfaces, and achieve dynamic control of material removal for extension to complex freeform surface geometries. The material removal rate for the femtosecond laser polishing experiments in FIGS. 10A-10B is on the order of $10^{-4}$ mm$^3$/min, comparable to certain ion-beam figuring processes with small beam sizes, used in final finishing of freeform optics. Using the metric of total deposited energy, laser-based material removal rate can be improved via determining an optimal combination of focal spot size, line overlap, scanning speed, and repetition rate, further competing with ultraprecision final-finishing techniques like magnetorheological finishing.

Example 7

Figure 11A:
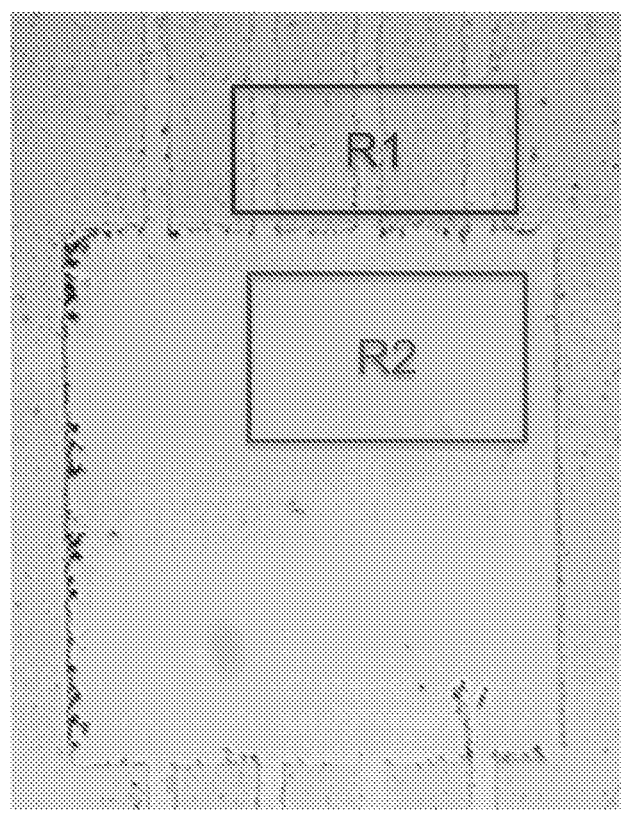
FIG. 11A shows a germanium substrate that has mid-spatial-frequency (MSF) pattern on the top and the laser polished portion in the bottom and FIG. 11B shows the peak to valley of the surface roughness for the laser polished area in comparison with the unpolished area.
Figure 11B:
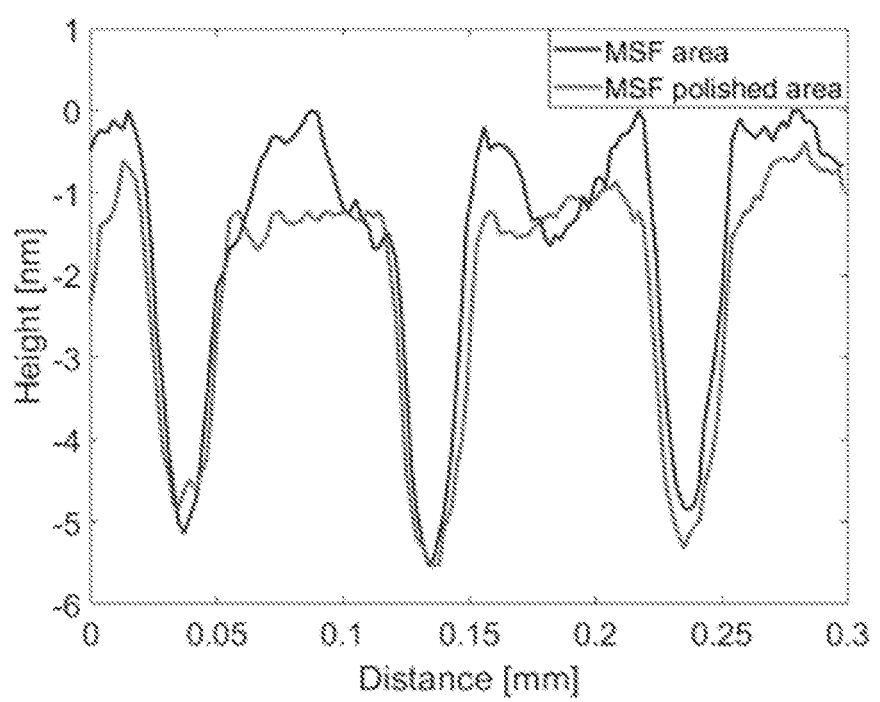

The effectiveness of using an ultrafast laser to mitigate mid-spatial frequency (MSF) pattern was tested. The same laser was used to generated MSF like periodic line pattern that has 100 nm spacing. An area scan was conducted to reduce the MSF pattern. FIG. 11A shows the germanium substrate that has an MSF pattern at the top and the laser polished portion at the bottom. R1 designates the area having an MSF pattern; R2 designates the laser polished area. FIG. 11B shows that the peak to valley of the surface roughness for the laser polished area R2 (after 20 area scans) is smaller that of substrate area R1 that was not polished (comparison of peak to valley of the MSF pattern without (blue) and with laser polishing (red)), indicating the effectiveness of ultrafast laser polishing on the mitigation of the MSF.

Example 8

Figure 12A:
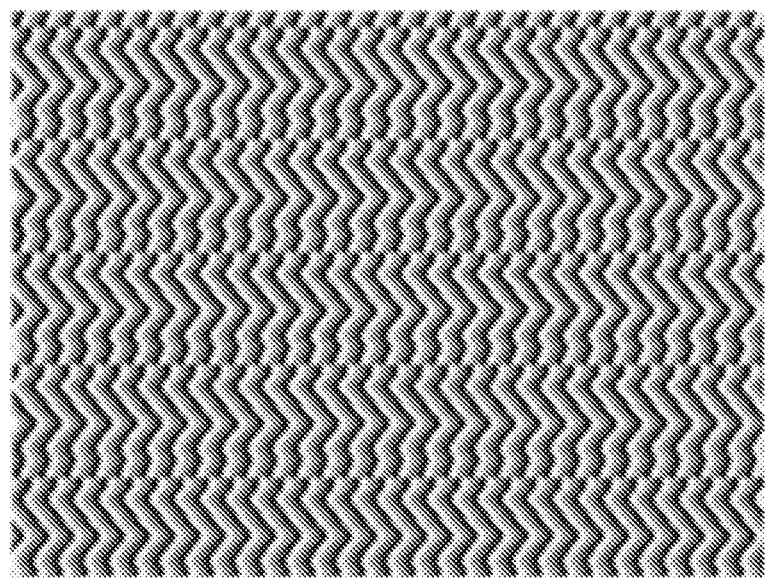
FIG. 12A shows a phase pattern generated on the spatial light modulator (SLM) surface and FIG. 12B shows the multiple focal spots that are generated by the SLM, which can be used to simultaneously figure/smooth the surface of a material.
Figure 12B:
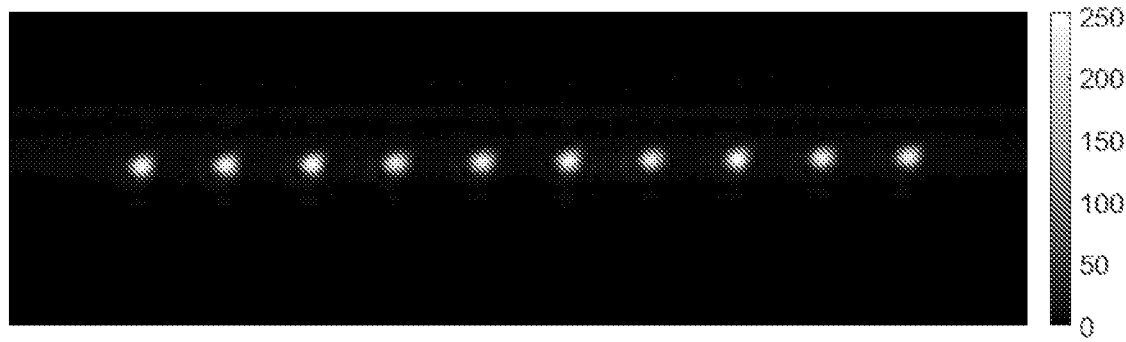

A spatial light modulator (SLM) and a phase retrieval algorithm (such as weighted Gerchberg-Saxton) were used to generate various phase patterns that can shape the laser pulse into desired spatial profiles, generating single/multiple beams with controlled spatial distribution and temporal delays to improve efficiency. FIG. 12A shows an illustrative phase pattern generated on the SLM surface and FIG. 12B shows an example for the multiple focal spots (nine uniform focal spots are produced) that can be used to simultaneously figure/smooth the surface of a material.

Example 9

Figure 13A:
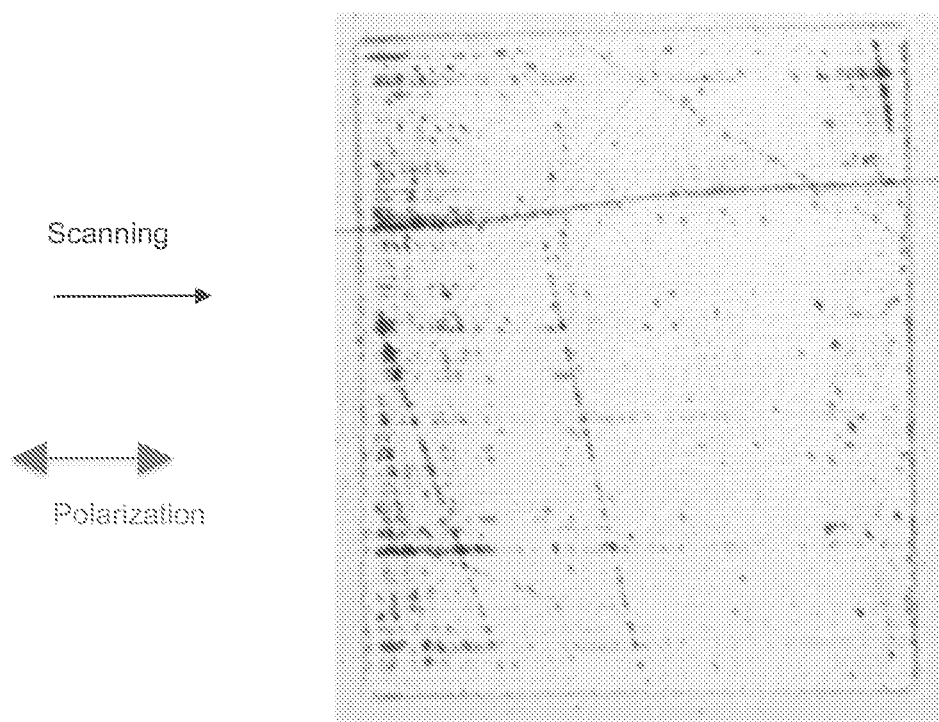
FIG. 13A shows surface smoothness achieved when the direction of the line scans is parallel to the laser polarization direction and FIG. 13B shows surface smoothness achieved when the direction of the line scans is orthogonal to the laser polarization direction.
Figure 13B:
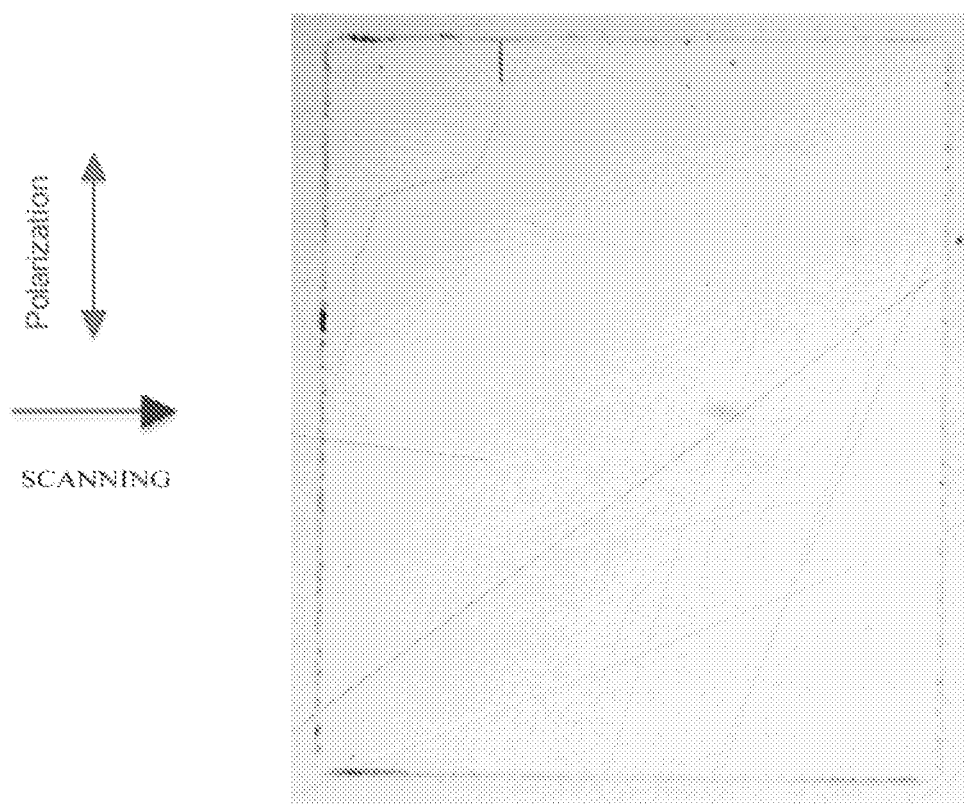

The orientation of the laser polarization in relation to the scanning direction can be adjusted to improve the quality of the surface smoothing. Smoothing includes removing mid-spatial frequency with single or sub-millimeter periodicity. This polishing experiment was done for two different polarizations, maintaining all other laser parameters and scanning parameters the same. FIG. 13A is an optical micrograph of the polished surface achieved when the direction of the line scans was parallel to the laser polarization direction and FIG. 13B is an optical micrograph of a polished surface achieved when the direction of the line scans was orthogonal to the laser polarization direction. A comparison shows that better surface smoothness is achieved when the direction of the line scans is orthogonal to the laser polarization direction as compared to when the direction is parallel.

EXAMPLE 10

In this example, we demonstrate a methodology, modeling, and experimental results for high-precision polishing of germanium using femtosecond lasers, i.e., selectively removing material while maintaining an optic-quality surface. In Section 1, we describe a strategy to achieve ablation and avoid the onset of undesired thermal effects by controlling the combined impact of laser parameters. A Two-Temperature Model was used to investigate the femtosecond laser/germanium interaction mechanism. Section 2 demonstrates that smooth and controllable laser polishing is achieved using a set of model-determined operational laser parameters. In Section 3, we discuss the potential underlying mechanism for femtosecond laser-based polishing of germanium.

1. Numerical Modeling to Determine Key Laser Parameters.

Numerical modeling of the femtosecond laser/germanium (Ge) interaction process was conducted to determine the potential laser parameters and processing conditions to achieve laser polishing. The modeling goal is to understand the individual and combined impact of laser parameters and to determine a combination capable of removing material with minimal thermal effects. The modeling process provides insight and guidance for targeted experiments, as experimental sensitivity studies with a broad parameter matrix are time-consuming and material expensive.

A three-dimensional Two-Temperature Model (TTM) was constructed to model scanning-based femtosecond laser processing of Ge. The TTM simulates how absorption of laser energy drives the generation of a dense, hot system of free-carrier electrons which then collides with and transfers heat to the material lattice until the systems reach thermal equilibrium. The model was used to investigate the sensitivity of the free-carrier electron density and the lattice temperature to different laser parameters. Simulating the free carrier density allows prediction of material breakdown and simulating the lattice temperature rise can predict the onset of thermal melting during processing.

In the TTM simulations, the laser pulse width and wavelength are 300 fs and 1030 nm. The initial Ge temperature was set to 300 K and the initial carrier density was set to $10^{13}$ cm$^{-3}$ to mimic the experimental processing environment and sample properties. The TTM equations and additional simulation/influence parameters are detailed in the Appendix.

1.1 Impact of Laser Fluence.

The TTM was first used to investigate the standalone impact of fluence during femtosecond laser/Ge interaction, as it can independently drive the onset of ablation and heating of the material surface. The pulse-induced free-carrier electron number density, carrier-system temperature, and lattice temperature were simulated to predict the potential onset of ablation and melting at different fluences.

FIG. 4 compares the TTM results for two different peak fluences: (FIG. 4A) 0.37 J/cm$^2$ and (FIG. 4B) 0.22 J/cm$^2$. For both fluence cases, the electron number density increases from an initial value of $10^{13}$ cm$^{-3}$ to the order of $10^{21}$ cm$^{-3}$ in less than one picosecond after the arrival of the peak intensity. This density is characteristic of the onset of material breakdown in semiconductors, indicating the potential onset of ablation for both cases. The generation of free-carrier electrons causes the electron-system temperature to rise to 29,000 K for a fluence of 0.37 J/cm$^2$ and to 16,000 K for a fluence of 0.22 J/cm$^2$. The earlier plateau in carrier temperature is due to competing mechanisms, such as heat capacity of carriers and the temporal gradient of carrier density. The higher electron temperature allows stronger coupling of thermal energy to the material lattice, causing the lattice temperature to rise to nearly 2100 K for the higher fluence, and ~1400 K for the lower fluence. Both predicted surface temperatures exceed the Ge melting temperature of 1213 K. The TTM does not simulate phase change, so for the lower fluence case, only the onset of melting, confined to nanometer-order depth, is predicted based on the amount of energy supplied to the simulated lattice voxel in comparison to the enthalpy of fusion for Ge (refer to Appendix).

1.2 Impact of Laser Repetition Rate and Scanning Speed.

To minimize the extent of heat accumulation, sufficient time must be allotted for heat diffusion to ensure that the surface can return near to its initial temperature prior to the next pulse incidence. The selected scan speed and repetition rate must control the temporal and spatial deposition of laser pulses to accommodate the material heat capacity and thermal conductivity.

The repetition rate and scan speed of our in-house femtosecond laser processing system can be nearly continuously tuned up to 2 MHz and 4 m/s. To avoid unbounded iterative numerical investigations, our previous numerical study of the impact of femtosecond laser parameters in semiconductor processing was consulted to identify operational ranges of scan speed and repetition rate to control heat accumulation. A laser repetition rate on the order of 100-500 kHz and a scan speed on the order of 1-4 m/s demonstrated the capability to minimize heat accumulation, achieve uniform processing conditions, and control the onset of thermal effects during femtosecond laser processing.

A 250-kHz repetition rate and a 1-m/s scan speed were initially selected for line-configuration processing. This set of laser parameters adheres to the numerically determined parameter ranges for low thermal impact processing in. It also enables a pulse overlap of 93% of the 1/e$^2$ focal-spot diameter (~60 µm), which is within the reported range for smooth processing.

The TTM was used to evaluate the capability of the identified laser parameters to control heat accumulation and the onset of thermal effects for polishing.

2. Laser Polishing Experiments and Results.

2.1 Experimental Validation of Laser Polishing Parameters.

See Example 5

2.2 Demonstration of Laser Polishing on Ge.

See Example 6

FIG. 8 compares an unprocessed (control) Ge surface and a laser-polished Ge surface generated using 20 polishing passes. The representative optical micrographs in FIGS. 8A and 8B show that the control surface contains defects including scratches and discoloration which are not evident in the laser-polished surface. FIG. 8C shows a surface height map of the 20-pass laser-polished area and the surrounding unprocessed surface. The depth of material removal in the polished area is 6 nm. The RMS roughness in both the surrounding unprocessed area and in the center of the laser-polished area are both 0.93 nm. This demonstrates that the devised laser polishing strategy is able to effectively remove surface defects while maintaining the sub-nanometer optic-quality surface roughness, revealing the capability of femtosecond laser polishing for high-precision material removal tasks.

3. Discussion on Polishing Mechanism.

The physical mechanism for achieving smooth polishing is attributed to high-precision laser ablation with controlled thermal impact. Ablation is predicted because the 0.22 J/cm$^2$ laser fluence is at the experimentally determined ablation threshold for Ge and the TTM-predicted number density rises to $10^{21}$ cm$^{-3}$ (FIGS. 4A-4C), characteristic of the onset of material breakdown in semiconductor materials. We expect that the onset of melting may also contribute to the smoothing mechanism since the TTM predicts that the 0.22 J/cm$^2$ fluence drives the surface temperature to slightly exceed the Ge melting point. However, only the onset of thermal melting, controlled to the nanometer order, is expected due to the small magnitude of the temperature rise/short time spent above the melting point (refer to Appendix). This high-precision melt-depth is a significant improvement over continuous-wave and micro/nanosecond-pulsed laser-based polishing strategies which generate melt/heat-affected zones with depths up to tens of micrometers.

Other laser-induced-breakdown phenomena could also play a role in laser polishing. For example, nonthermal melting and/or laser annealing can cause lattice ordering/disordering in single-crystal semiconductors, potentially contributing to smoothing the Ge surface. These phenomena can occur once approximately ten percent of the valence band electrons have been promoted to the conduction band, signified by electron densities in the range of $10^{21}$-$10^{22}$ cm$^{-3}$, consistent with the TTM-predicted electron densities in Section 2. However, the TTM cannot independently assess or differentiate these phenomena from ablation-based material removal.

CONCLUSION

A strategy for polishing of Ge was established to precisely remove material while maintaining optical surface quality. A TTM of scanning femtosecond laser processing was built to investigate the combined impact of laser parameters on Ge ablation and surface temperature. Using the model, we successfully determined a set of laser polishing parameters which produce controlled ablation and minimized thermal effects on the Ge surface, validated by experiments. For the first time, to our knowledge, we demonstrated femtosecond-laser-based polishing of Ge with tunable material removal and maintained the optic-quality surface with roughness of ~1 nm. We also established a metric to scale-up the material removal towards larger polishing tasks and non-flat surfaces.

APPENDIX

Two-temperature model formulation.

The TTM of scanning, multi-pulse femtosecond laser-material interaction presented in Section 2 was based on a model originally formulated to simulate femtosecond laser processing of silicon. Adapting the model for Ge required identification and integration of material properties to effectively account for its electronic and thermal behaviors and re-derivation of certain equations to accommodate these changes; the original numerical algorithm was maintained. Therefore, this Appendix only describes relevant TTM modifications to simulate Ge. We direct the reader to our separate publication for information on the algorithm, L. L. Taylor, R. E. Scott, and J. Qiao, "Integrating two-temperature and classical heat accumulation models to predict femtosecond laser processing of silicon," Opt. Mater. Express 8, 648-658 (2018).

The TTM simulates the following phenomena for each incident laser pulse: (1) absorption of laser pulse energy, (2) generation of free-carrier electrons, (3) temperature of the electron system, and (4) temperature of the material lattice. These phenomena are respectively described by Eqs. 1-4. The key parameters and coefficients for all equations are detailed in Table 1.

When a laser pulse is incident on a material, a fraction of the energy is reflected away (R=0.39 for NIR light on Ge) and the remainder of the energy is absorbed by the bulk.

$$dI/dz = -(\alpha + \Theta N_c)I \quad (1)$$

Equation 1 describes the fall-off of intensity along the direction of laser propagation due to energy absorption. When irradiating Ge with 1030-nm light, linear absorption ($\alpha$) dominates since the photon energy is much higher than the material bandgap ($E_{photon}$=1.2 eV; $E_{gap}$≈0.8 eV). Energy absorption drives the number density of generated free-carrier electrons, $N_c$, orders of magnitude above its initial, intrinsic value of $10^{13}$ cm$^{-3}$, so free-carrier absorption ($\Theta N_c$) also plays a role. The impact of two-photon absorption is negligible when $E_{photon} \gg E_{gap}$, therefore, it is not considered in this model.

$$\frac{\partial N_c}{\partial t} = \frac{\alpha I}{E_{photon}} - \gamma N_c^3 - \nabla \cdot \vec{J} \quad (2)$$

Equation 2 shows that the number density of free-carrier electrons is increased by energy absorption and respectively decreased by Auger recombination and ambipolar diffusion. Impact ionization is not considered because it is negligible in comparison to the dominant effect of linear absorption.

$$C_{e-h}\frac{\partial T_c}{\partial t} = (\alpha + \theta N_c)I - \left[\frac{C_{e-h}}{\tau}(T_c - T_l) + \nabla \cdot \vec{W} + \frac{\partial N_c}{\partial t} \cdot (E_{gap} + 3k_bT_c) + \frac{\partial E_{gap}}{\partial t} \cdot N_c\right] \quad (3)$$

Equation 3 describes the corresponding temperature of the carrier system, increased by energy absorption and decreased by coupling of thermal energy from the carriers ($T_c$) to the lattice ($T_l$) according to the electronic heat capacity ($C_{e-h}$) and relaxation time ($\tau$), ambipolar energy current ($\overline{W}$), and respective changes in kinetic and bandgap energies (where, $k_b$ is the Boltzmann constant).

$$C_l \frac{\partial T_l}{\partial t} = \frac{C_{e-h}}{\tau}(T_c - T_l) + \nabla \cdot (\kappa_l \nabla T_l) \quad (4)$$

Equation 4 describes the evolution of the lattice temperature throughout the laser-material interaction process. Thermal energy from the carrier system is coupled to the lattice until the systems reach thermal equilibrium. Upon thermalization, Eq. 4 becomes the classical heat conduction equation which describes bulk heat diffusion according to the material heat capacity ($C_l$) and thermal conductivity ($\kappa_L$) in the time between laser pulses.

TABLE 1

Key parameters for the Ge TTM

| Parameter | Symbol | Value | Unit |
|---|---|---|---|
| Photon energy ($\lambda$ = 1030 nm) | $E_{photon}$ | 1.2 | eV |
| Bandgap Energy | $E_{gap}$ | $0.803 - 3.9 \times 10^{-4} \cdot T_l$ | eV |
| Linear absorption coefficient | $\alpha$ | $1.4 \times 10^4 \cdot (1 + T_l/2000)$ | cm$^{-1}$ |
| Free-carrier absorption cross-section | $\Theta$ | $6.6 \times 10^{-20}$ | cm$^2$ |
| Auger recombination coefficient | $\gamma$ | $2 \times 10^{-31}$ | cm$^6$/s |
| Ambipolar diffusion coefficient† | D | $65 \cdot (T_l/300)^{-1.5}$ | cm$^2$/s |
| Electron relaxation time | $\tau$ | $400 \cdot \left(1 + \left(\frac{N_c}{2 \times 10^{21}}\right)^2\right)$ | fs |
| Electronic heat capacity | $C_{e-h}$ | $3N_c k_b$ | J/(cm$^3 \cdot$ K) |
| Lattice heat capacity | $C_l$ | $1.7 \cdot (1 + T_l/6000)$ | J/(cm$^3 \cdot$ K) |
| Lattice thermal conductivity | $\kappa_l$ | $675 \cdot T_l^{-1.23}$ | W/(cm $\cdot$ K) |

†Related to J, W

Influence parameters.

An exploration of the influence of the free-carrier absorption cross section and electron relaxation time on the simulation results was conducted to address the wide range of values reported in the literature. For each of the investigated influence parameter values, the behavior of the TTM-predicted electron number density, electron temperature, and lattice temperature were compared to the results of molecular dynamics (MD) simulations of femtosecond laser/Ge interaction. The free-carrier absorption cross section and electron relaxation time in Table 1 were selected for the model because they enable the number density and temperatures to rise and fall to similar orders of magnitude on consistent timescales with the MD simulations.

Prediction of thermal melting.

Although the TTM can predict the surface temperature rise in the material lattice, it does not simulate solid/liquid phase change. Therefore, the surface temperature prediction is treated only as an indication of thermal energy transfer to the lattice. In order for the laser to thermally melt the material surface, enough energy must be supplied after the melting point has been reached to overcome the enthalpy of fusion required for solid-liquid phase change (36.94 kJ/mol for Ge). In a TTM lattice voxel with dimensions of 2 µm×2 µm×5 nm, this would correspond to an energy of ~50 pJ, calculated as $\Delta E = (T_{TTM} - T_{melt}) \cdot c_v V$, where $T_{TTM}$ is the TTM-predicted lattice temperature, V is the voxel volume, $T_{melt}$ is the Ge melting temperature, and $c_v$ is the volumetric specific heat capacity. For the 0.22 J/cm$^2$ simulation in Section 2, the energy supplied to the surface voxel after the melting point is reached is just 9 pJ, less than 20% of the energy required for full melting. Hence, we predict only the onset of thermal melting at the surface, and that the melt depth is constrained to the single-digit nanometer order.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for a non-contact ultrafast laser-based removal, simultaneously achieving figuring and smoothing of a material surface, comprising:
   collecting thermal and electron properties of a material;
   modeling how absorption of laser energy by the material drives the generation of a dense, hot system of free-carrier electrons and the rise of material lattice temperature;
   determining a laser ablation threshold for the material;
   determining the material surface temperature at the laser ablation threshold;
   modeling multipulse laser-induced temperature evolution and free-electron density evolution at the material surface at a laser fluence near the laser ablation threshold for a range of repetition rates and scanning speeds to establish a baseline of laser parameters for line scans;
   experimentally optimizing the baseline laser parameters which ablate the material and control thermal impact on the surface of the material to achieve a surface roughness of less than 10 nanometers;
   experimentally optimizing a scanning strategy for area scans comprising the starting position and percentage overlap of the line scans to minimize surface scan marks;
   determining a number of area scans to achieve a predetermined material removal depth at a specific location; and
   scanning a surface of the material with an ultrafast laser beam operating within the optimized baseline parameters and the optimized starting position, percentage overlap of line scans and number of area scans which simultaneously ablate the material to the predetermined material removal depth while maintaining the surface roughness of less than 10 nanometers.

2. The method of claim 1, wherein the laser parameters includes at least one of a range of wavelength of from 248 nm to 2400 nm, a range of pulse duration of from 50 fs to 50 ps, and a range of laser repetition rate of from 100 Kilohertz to 1 Gigahertz.

3. The method of claim 1, wherein the laser parameters for line scans includes at least one of wavelength, pulse length, fluence, repetition rate, scanning speed, and polarization.

4. The method of claim 1, wherein the area scanning strategy includes at least one of a laser repetition rate, scanning speed, overlap for line scans, number of area scans, scanning direction in relation to the laser polarization and dithering method.

5. The method of claim 1, wherein the scanning comprises a laser fluence near the ablation threshold of the material at a predetermined pulse duration, repetition rate, and scanning speed with a line scan overlap between 50% to 85%.

6. The method of claim 4, wherein the scanning direction of the laser beam is orthogonal to the direction of laser polarization.

7. The method of claim 1, wherein the surface of the material is flat, curved, or freeform.

8. The method of claim 1, wherein the scanning comprises surface figuring by removing a predetermined thickness of the material in different spatial locations to make a predetermined shape.

9. The method of claim 1, wherein the scanning comprises surface smoothing by removing tool patterns having periodical mid-spatial frequency.

10. The method of claim 1, wherein the scanning strategy for area scans comprises:

randomizing a starting position for each area scan following a first of multiple area scans, by spatially dithering the starting position of each line scan in a direction orthogonal to a line scanning direction so that the line scans of multiple area scans do not overlap with each other eliminating ripples otherwise induced by exact overlay of line patterns from multiple area scans.

11. A system for non-contact ultrafast laser-based removal, simultaneously achieving figuring and smoothing of a material surface, including: according to the method of claim 1, an ultrafast laser;

a beam delivery system configured to guide a beam from the laser to the material surface;

a beam shaping system configured to generate a spatial, temporal fluence distribution or energy deposition of the beam at the material surface;

a sample fixture and positioning stage; and a beam scanning system having timing synchronized with the laser beam and the sample fixture and positioning stage.

12. The system of claim 11, wherein the ultrafast laser comprises a femtosecond or picosecond laser, having a pulse duration of less than 50 picoseconds.

13. The system of claim 11, wherein the control module contains a physical model which comprises a Two Temperature Model (TTM) or a Nonlinear Absorption Model (NAM) in combination with a Heat Accumulation Model (HAM).

14. The system of claim 11, wherein the material comprises germanium, silicon, metal, glass, crystal, ceramic, polymer, optical or additively manufactured material.

15. The system of claim 11, wherein the surface of the material is flat, curved, or freeform.

16. The system of claim 11, wherein the ultrafast laser is configured for initially shaping or polishing of an optic preform to finishing of the preform.

17. The system of claim 11, wherein the ultrafast laser is configured for performing inter-layer smoothing or densification and final surface polishing of the material.

18. The system of claim 11, wherein the ultrafast laser is configured for providing integrated optics, micro-optics, or photonics.

19. The system of claim 11, further comprising an extraction system configured to remove ablated nanoparticles from the surface of the sample.

* * * * *